United States Patent
Ward

(10) Patent No.: US 10,504,198 B1
(45) Date of Patent: Dec. 10, 2019

(54) LONGITUDINAL MULTI-AUTHOR CARE PLANNING AND MANAGEMENT SYSTEM WITH USER-TAILORED CARE PLAN HIERARCHY THAT PROPAGATES BASED ON CARE RESPONSIBILITY INFORMATION

(71) Applicant: Reward Health Sciences, Inc., Windson (CA)

(72) Inventor: Richard E. Ward, Windsor (CA)

(73) Assignee: Reward Health Sciences, Inc., Windsor (CA)

( * ) Notice: Subject to any disclaimer, the term of this patent is extended or adjusted under 35 U.S.C. 154(b) by 517 days.

(21) Appl. No.: 15/170,898

(22) Filed: Jun. 1, 2016

Related U.S. Application Data

(63) Continuation of application No. 13/843,098, filed on Mar. 15, 2013, now abandoned.

(51) Int. Cl.
*G06Q 50/22* (2018.01)
*G06Q 10/10* (2012.01)
*H04L 29/06* (2006.01)

(52) U.S. Cl.
CPC ............ *G06Q 50/22* (2013.01); *G06Q 10/10* (2013.01); *H04L 67/42* (2013.01)

(58) Field of Classification Search
CPC ........ G06F 159/00; G06F 17/60; G06Q 50/00
USPC ......................................................... 705/3, 2
See application file for complete search history.

(56) References Cited

U.S. PATENT DOCUMENTS

| | | | | |
|---|---|---|---|---|
| 5,802,495 A | * | 9/1998 | Goltra | G06F 17/2229 705/3 |
| 6,434,531 B1 | * | 8/2002 | Lancelot | G06F 19/325 705/3 |
| 7,020,618 B1 | | 3/2006 | Ward | |
| 7,707,057 B2 | | 4/2010 | Ward | |

(Continued)

OTHER PUBLICATIONS

Introducing EpicCare Ambulatory and Practice Management System, Yale New Haven Health, 2012.

(Continued)

*Primary Examiner* — Dilek B Cobanoglu
(74) *Attorney, Agent, or Firm* — Pillsbury Winthrop Shaw Pittman LLP

(57) ABSTRACT

A method and system for care planning and management that provides a patient-centered single source of truth to foster teamwork and improved quality of care. The system facilitates creation of multi-author structured care plans through derivation of care relationships, care responsibilities and care plan elements to pre-populate care plans, and uses a hierarchical topic catalog and associated structured sentence templates and care plan templates to facilitate the completion of care plans. It aids interdisciplinary input through workflow-enabled routing of draft care plans, and rules-driven co-signing. The system allows each of multiple authors to separately tailor the sort order, hierarchy and information prominence of care plan structured sentences. The system uses care relationship and care responsibility information to optimize the propagation of care plan view tailoring instructions among co-authors. Finally, the system facilitates care plan execution using workflow automation technology to track and coordinate the process of delivering each ordered service.

25 Claims, 17 Drawing Sheets

(56) References Cited

U.S. PATENT DOCUMENTS

| | | | | |
|---|---|---|---|---|
| 7,742,931 | B2* | 6/2010 | McElwain Miller | G06F 17/243 705/2 |
| 8,346,698 | B2* | 1/2013 | Baluta | G06Q 10/087 706/45 |
| 2003/0036927 | A1* | 2/2003 | Bowen | G06Q 40/08 705/4 |
| 2003/0050801 | A1* | 3/2003 | Ries | G06F 19/3481 705/2 |
| 2005/0202383 | A1* | 9/2005 | Thomas | G06Q 50/22 434/262 |

OTHER PUBLICATIONS

Wellcentive EHR-MU Receives ONC-ATCD 2011/2012 Certification, Wellcentive News, Nov. 16, 2011.
Casenet Announces Release 4.5 of its Innovative TruCare Care Management Platform, prweb.com, Jun. 10, 2011.
Test Procedure for §170.306(a) Computerized Provider Order Entry, Aug. 13, 2010.
Test Procedure for §170.302(c) Maintain up-to-date problem list, Aug. 13, 2010.
Approved Test Procedures Version 1.0, Healthcare.nist.gov, Feb. 7, 2011.

\* cited by examiner

300

− Abdominal pain, Complaint: "Stomach is hurting me at night,"
Onset 10-01-11, CR: Christopher Cooper, MD <more>

Differential Diagnoses:

310
- Gastroenteritis
- PUD
- Pancreatitis
- Cholecystitis
- Diverticulitis
- UTI 330
- ☐ NPO apart from meds
- ☐ IVF, D5 1/2 NS at 125 cc/hr x 2 L
- ☐ EKG in AM
- ☐ Urine C+S
- ☐ Morphine 2 mg IV q 2-4 hr PRN pain
- ☐ Liver/gallbladder U/S
- ☐ CT abdomen (with or without PO and IV contrast)
- ☐ GI consult
- ☐ CBCD, CMP in AM

FIG. 3

LONGITUDINAL MULTI-AUTHOR CARE PLANNING AND MANAGEMENT SYSTEM WITH USER-TAILORED CARE PLAN HIERARCHY THAT PROPAGATES BASED ON CARE RESPONSIBILITY INFORMATION

CROSS-REFERENCE TO RELATED APPLICATIONS

This application is a continuation of U.S. Non Provisional application Ser. No. 13/843,098 filed Mar. 15, 2013, incorporated in its entirety herein.

FIELD OF THE RELATED ART

This application relates to health care information technology, and even more particularly to clinical documentation and care management systems.

DESCRIPTION OF THE RELATED ART

Health care providers require planning and coordination of services across multiple members of a clinical team. This is particularly true in the care of patients that have multiple concurrent chronic and acute medical problems or severe illnesses requiring extensive diagnostic tests and complex multi-modality treatment protocols. Such patients require care from numerous care providers, including primary care physicians, specialist physicians, nurses and a diverse collection of allied healthcare professional practices in multiple acute care and ambulatory care settings, as well as informal care-givers such as family members. Such patients are becoming more common as the populations ages, and more patients are living longer and sicker.

The lack of coordination of care within the healthcare system has been broadly recognized as a longstanding problem, and numerous healthcare organizations have launched efforts to improve clinical integration, and private and public payers have launched various reimbursement changes intended to incentivize such clinical integration efforts. Such efforts are variously described as accountable care organizations (ACOs), organized systems of care (OSCs), integrated delivery systems, and managed care. The efforts to improve the coordination of care and clinical integration across the healthcare delivery system have led health care provider organizations to invest in new clinical information systems, new population-oriented analytic systems, and new human resources such as nurses playing roles variously described as care management, case management, care coordination, disease management, health navigation, wellness coaching, etc.

To support these invigorated efforts to improve the coordination of increasingly complex care, health care providers require health information technology that goes beyond the traditional function of "recordkeeping" and "information exchange," which have been the focus of mainstream clinical information technologies such as electronic health records (EHR) technology and health information exchange (HIE) technology, respectively. Conventional EHR and HIE technology has provided important incremental benefits, particularly in the form of improving access to health information across providers and alerting providers to gaps in evidence-based services. But, such technology has been disappointing in terms of its ability to support substantial changes in the fundamental processes of clinical reasoning, gathering multi-disciplinary input, and coordinating and tracking potentially complex protocols across multiple providers in multiple settings over time. And, even though EHR and HIE technology has succeeded in increasing access to the numerous clinical documents that contain information relevant to the plan of care of a particular patient, such technology has not addressed the need for a single, comprehensive source of truth for care plan information. Clinicians routinely author care plan information as part of encounter documents that are authored by a single clinician at a single point in time. When a patient sees a second clinician, another care plan is generated that may or may not include the information from the prior clinician's encounter note. When the patient returns back to see the first clinician, yet another plan of care is authored, which may or may not reflect the information in either of the prior two encounter notes. In addition to the encounter notes, additional care plan-related information is created in prescription forms, diagnostic test requisitions, referral authorizations, discharge summaries, and numerous other types of clinical and administrative documents and datasets. For patients with multiple chronic and acute conditions or severe conditions, who are receiving services from dozens of clinicians, the problem is greatly magnified, even in the rare case where all of those diverse documents containing care plan information are conveniently available in an EMR or through and HIE system.

As with any process that requires teamwork, it is essential for team members to have clearly defined roles and responsibilities so as to avoid wasteful duplication of effort and errors of omission where multiple team members assumed others were responsible for an important clinical task. Since the many clinical team members involved in the care of a single patient are delivering care in diverse, hectic settings, there is a need for information technology to facilitate an efficient process for keeping track of which clinicians are playing which roles in the care of the patient, and which clinicians are taking primary responsibility for assuring the particular patient problems are addressed and particular steps in the process of delivering ordered services are carried out.

Furthermore, as the cost of care continues to increase, both in absolute terms and as a share of the economy, health care providers who are bearing increasing economic risk for the total cost of care, are increasing their use of prospective review and prior authorization of health care services. However, such utilization management process are perceived as intrusive and offensive by providers, who resent when what they consider to be their final clinical decisions are overturned by distant people who do not have the full context of the case. Health care organizations need better ways to provide meaningful oversight over the cost and quality of care using processes that feel less like second-guessing and more respectful, collaborative, informed and helpful.

A number of healthcare information technologies have been developed that attempt to address different aspects of these challenges. Document imaging, optical character recognition, voice recognition and natural language processing technologies have been developed to reduce the data entry burden on busy clinicians attempting to capture clinical documentation, including care plan elements. These technologies have been helpful to improve information access to information that was not previously captures on a timely basis or in an electronic form, and they are able to capture some structured data elements that are useful for case finding. But, such methods have been insufficiently interactive to permit them to be employed to consistently capture highly structured care plan data across diverse members of a clinical team in a manner which assures the complete capture of specific data elements. Computer-based Order Entry (COE) systems have been developed to capture orders, and ePrescribing systems have been developed to capture prescriptions (a type of order). Many COE and ePrescribing systems include the ability to use order sets to reduce data entry burden and to promote standardization of clinical practice. Many COE and ePrescribing systems also offer some clinical decision support features, such as prompts for gaps in care or alerts regarding problems with proposed orders. But, such COE and ePrescribing systems are not designed to capture all types of information related to care plans, such as goals, barriers, nursing interventions, etc. Template charting technology has been developed, originally by companies such as Purkinje and Oceania. Template charting technology introduced the concept of structured sentences as a flexible data structure used to represent data that is both computer readable and clinician readable. This technology also offers the benefits of being able to create a template that can reduce the burden of data entry and increase the consistency of capture of specific data elements and the consistency of clinical practice. Template charting functionality within EHR systems has improved the ability of EMRs to support structured data capture as needed to support simple clinical decision support and subsequent population-level analytics. Care Management applications were developed primarily for use by nurse care managers employed by health plans or care management vendors hired by health plans. Care Management applications included the concept of structured care plans with hierarchical relationships among such care plan elements as issues, action, outcomes, barriers, and outcomes. Care Management applications include the ability to use care plan templates and some are designed to support the use of a single care plan data structure intended to be updated over time by multiple users (i.e. a multi-authorship longitudinal care plan). However, such care management applications have not been successfully employed for use by multiple authors across diverse professions, and specifically not used on an ongoing basis on a large scale for longitudinal care plans co-authored by nurses, primary care physicians and physician specialists.

In U.S. Pat. Nos. 7,020,618 and 7,707,057, and are expressly incorporated by reference herein, we disclosed a method and system for customer service process management which was designed to be useful for care planning and management. This technology is designed to support the use of structured templates to assist clinician users in the creation of structured care plans intended to be updated over time by multiple members of the clinical team (e.g. multi-authorship longitudinal structured care plans). The technology is designed to offer clinical decision support during the care plan authoring process, to create a custom view of the care plan optimized for sharing with the patient, the use of workflow automation technology to facilitate the process of gathering multi-disciplinary input into the draft care plans, and the use of workflow automation technology to coordinate and track the execution of each of the ordered services contained in the care plan through multiple steps of execution.

These various types of systems have provided great benefits for patient care, and have been implemented in a variety of settings for clinicians in various roles, there is an opportunity to reduce barriers to the realization of a single patient-centered care plan utilized across settings and professions to achieve the benefits of improved clinical reasoning and improved quality and efficiency of care.

SUMMARY

In view of the above, an object is to reduce the effort required to enter care plan information and to reduce the likelihood of missing important care plan elements documented in various external systems. Another object is to reduce the degree of irrelevant information that a clinician faces when interacting with care plan information created by other members of the clinical team from different professional disciplines and specializations and that are emphasizing different aspects of the holistic care of a particular patient. Still another object is to reduce data structure limitations that frustrate clinicians efforts to create clinical documentation of care planning information in ways that reflect the clinician's clinical thinking and conceptualization of the case, while still maintaining sufficient limitations to ensure the integrity and clinical meaningfulness of the care plan. Another object is to reduce the degree that peer review is perceived as inconvenient or offensive second-guessing. And, finally, an object is to anticipate and accommodate a potentially lengthy transition period when some of the clinicians within a provider network are farther along than others in their adoption of more collaborative care models for care planning and care management.

These and other objects and advantages are obtained by providing for methods and systems for care planning and management. In one embodiment, the system includes at least one client computer used by members of the clinical team and at least one client computer used by patients, which are each interconnected via a communication network to certain one or more database service computers, one or more workflow automation server computers, one or more external server computers.

In a specific embodiment of the system, the system can be used by clinician users to create a structured care plan for a patient, specifying whether that care plan is intended to be created at a point-in-time or intended to be updated over time (a "longitudinal" care plan), and specifying whether the care plan is to be authored by a single clinician, by a limited number of invited co-authors, or by all clinician users involved in the care of the patient (an "open authorship" care plan). To reduce the burden of authoring the care plan on clinician users, the system allows care plans to be created using care plan templates, each consisting of a collection of structured sentenced templates and each associated with nodes in a hierarchical topic catalog that makes it easy for a clinician user to find care plan templates that are relevant to the patient and conveniently add multiple relevant structured sentences to the care plan as proposed node that are inserted in the care plan in a clinically-meaningful and intuitive location. To further reduce the burden of authoring, the system is able to extract care plan elements from external clinical and administrative systems and from other co-existing structured care plans within the system in order to offer proposed nodes for the clinician user to consider for inclusion without requiring data entry.

The methods and systems described also allow for clinician users to create clinician-tailored views of specific care plans for specific patients. A objection to multi-disciplinary multi-author "team", care plans has been that clinicians are reluctant to "wade through" a lot of information entered by co-authors that seems irrelevant to their work, and reluctant to give up the ability to create a care plan that is structured and organized so as to reflect their clinical thinking and the aspects of the case upon which they are focusing. To reduce these barriers to adopting multi-disciplinary multi-author care planning, the system allows each clinician co-author to make changes to the ordering and hierarchy of information within the care plan, and to change formatting parameters that increase the prominence of different parts of the care plans. Clinicians can also benefit from being able to view the same care plan through different "eyes"—using standard views that organize the care plan different ways, and by viewing the clinician-tailored views of other members of the clinical team.

In another aspect, the methods and systems allow for the members of the clinical team to unambiguously document and communicate the care relationships between patients and clinicians, and, notably, which clinicians have accepted "care responsibility" for each of the patient's problems. The system reduces the burden of creating and maintaining such granular care responsibility information by being able to derive care responsibilities from data extracted from external systems, and by managing care responsibility as an integral part of structured care plans. The system then leverages this care relationship and care responsibility information by permitting configurable rules that use this information to control how clinician-specific tailoring of care plans is propagated, or not, to the care plan views of other clinicians. For example, the system permits tailoring instructions made by the primary care physician (based on care relationship data), or tailoring instructions made with a problem by the clinician that has accepted care responsibility for the problem to be propagated to the views other clinicians involved in the case, while other user's tailoring instructions affect only their own view of the care plan.

The system also facilitates the gathering of interdisciplinary input and the process of clinical oversight, such as between attending physicians and residents, physicians and allied heath professionals, peer reviewers and pre-authorization clinical reviewers, Finally, the system is designed to support population health management, patient engagement, and clinical workflow management.

BRIEF DESCRIPTION OF DRAWINGS

The above and other objects, features and advantages are further described in the detailed description which follows, with reference to the drawings by way of non-limiting exemplary embodiments, wherein like reference numerals represent similar parts throughout several views and wherein:

FIG. 3 is a diagram representing a the appearance of a portion of a structured care plan in a computer display FIG. 17 is a process flow diagram explaining the steps for

DETAILED DESCRIPTION OF THE PRESENTLY PREFERRED EMBODIMENTS

The figures depict a preferred embodiment for purposes of illustration only. One skilled in the art will readily recognize from the following discussion that alternative embodiments of the structures and methods illustrated herein may be employed without departing from the principles described herein.

Figure 1:
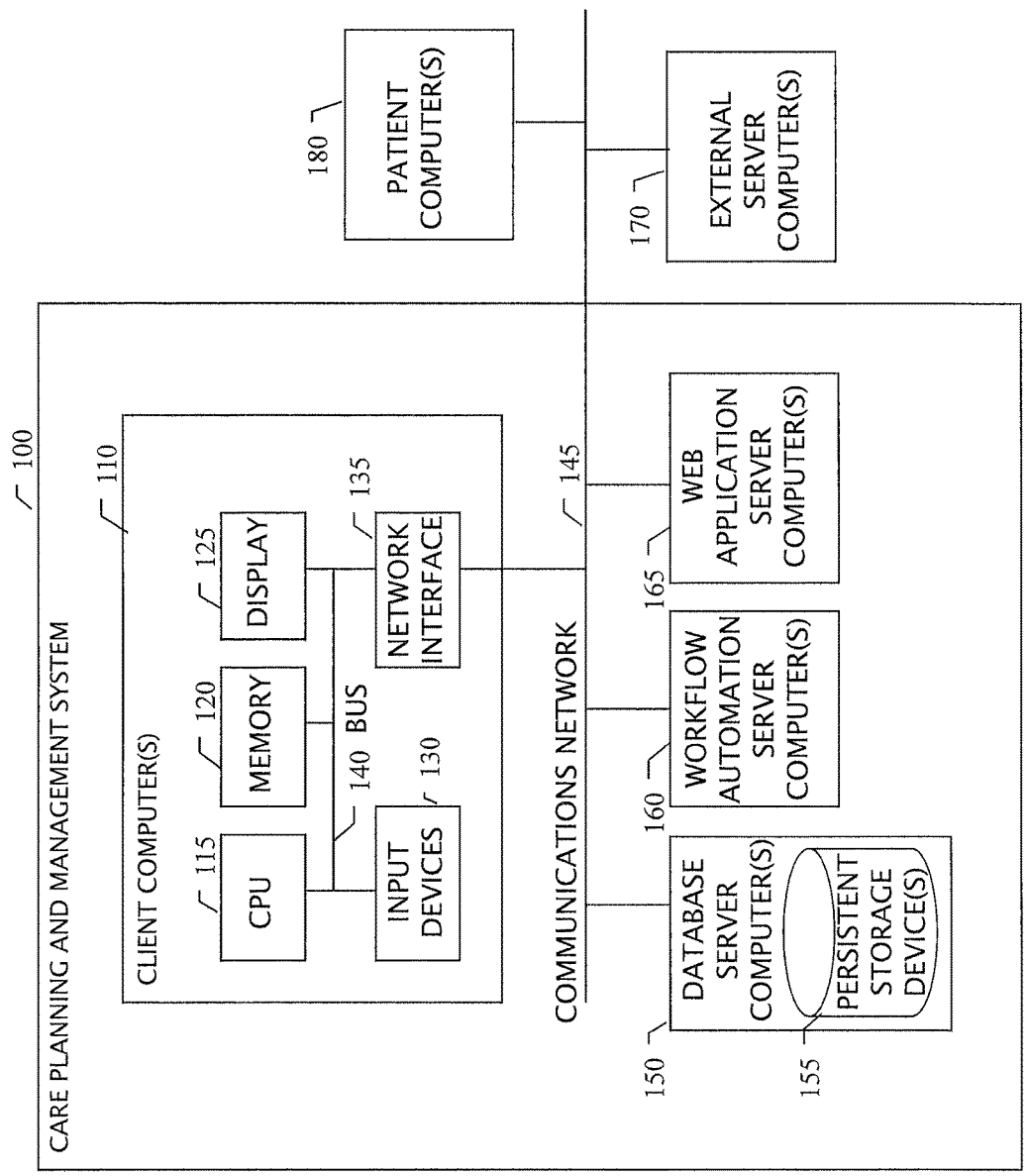
FIG. 1 is a block diagram of a computer-based system for care planning and management.

Referring to FIG. 1, there is shown a system 100 for managing customer service processes. The major components of system 100 include at least one client computer 110, such as a desktop personal computer, a laptop computer, or a portable tablet or smartphone device containing a central processing unit (CPU) 115, memory 120, at least one display device 125, at least one input device 130 (such as a keyboard and a mouse pointing device), and a network interface 135. These components of the client computer 110 are interconnected via a bus 140. Program instructions are stored in memory 120, allowing the computer to perform in the manner detailed below. Clinician users and patients directly interact with client computers such as the one illustrated as 110. The network interface 135 provides a means for communication between the client computer 110 and other computers on a communications network 145. The system 100 also includes one or more database server computers 150 for storing health information, system configuration data and rules, one or more workflow automation server computers 160, and one or more web application server computers 165. Application programs, each containing program instructions correlated to the necessary functions being performed, are stored in corresponding memories for these computers and servers, to perform in the manner detailed below. Each of these computers is of conventional design, with internal components as generally described for the client computer 110. The database server computer(s) 150 includes one or more persistent storage devices 155, such as a hard disk drive. These computers may also be interconnected via communications network 145 to one or more external server computers 170, such as computers used for legacy systems within the various organizations involved in the health care delivery process. It should be noted that, although FIG. 1 illustrates the use of a single, separate computer serving as each of the client computer 110, database server computer 150, workflow automation server computer 160, web application server computer 165 and external server computer 170, many other embodiments are possible. In accordance with conventional network computing methods, several of these computer functions could be run on a single physical computer device. Alternatively, several of these computer functions could be distributed to be run on a plurality of physical computer devices. Also shown is one or more patient computers 180, which can remotely contact the single separate computer, preferably via the Internet, to provide and receive information as discussed hereinafter.

Figure 2:
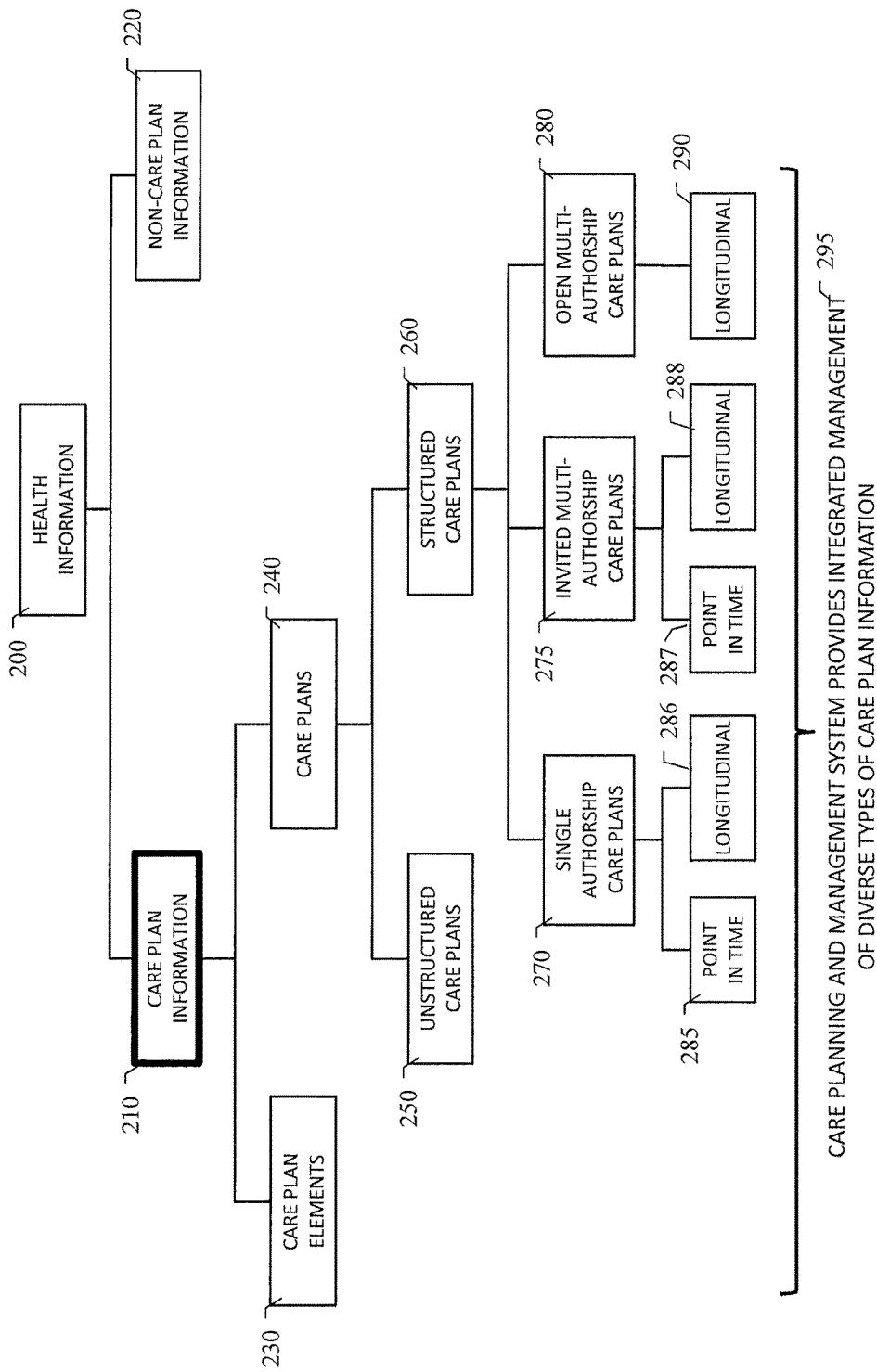
FIG. 2 is a diagram depicting a taxonomy of health information, with an emphasis on care plan information

Referring now to FIG. 2, the taxonomy of health care information is illustrated so as to clarify the terminology used herein. Care plan information 210 is a subset of health information 200. Care plan information includes care plan elements 230 that can be found in various systems that are external. For example, diagnosis codes and procedure codes can be found in claims records, hospital discharge summaries, analytic databases, disease registries, and electronic health record systems, among others. Problems can be found within problem lists of electronic health record systems, health risk appraisal systems, and health plans' care management systems. Issues, actions, and outcomes may be found with external care management systems. Data regarding the health care providers who care for the patient can be found in the form of assigned primary care physician identifiers within the membership systems of health maintenance organizations, in provider lists within some electronic health record systems and clinic practice management systems, on admit-discharge-transfer system records, and other sources.

In addition to care plan elements, care plan information also includes complete care plans 240. Some care plans take the form of unstructured electronic documents 250, such as documents created using a conventional word processing application or document image files created by scanning handwritten care plan records. Other care plans take the form of structured care plans 260, which are represented in the form of coded elements that can facilitate manipulation by information systems.

Turning to FIG. 3, a diagram is provided to illustrate the appearance of a structured care plan as part of the user interface display of a preferred embodiment. In this example, the structure care plan appears on the user interface to be conventional unstructured text, as might be created in a conventional word processing application. However, such a structured care plan is comprised of a hierarchy of care plan nodes, where some of those nodes are associated with structured sentence data item (also described herein as a "structured sentence," or "SS"), such as a structured sentence documenting the symptom of abdominal pain 300, a structured sentence documenting a diagnosis, gastroenteritis 310, and a structured sentence documenting an order for a drug, morphine 330.

Figure 4:
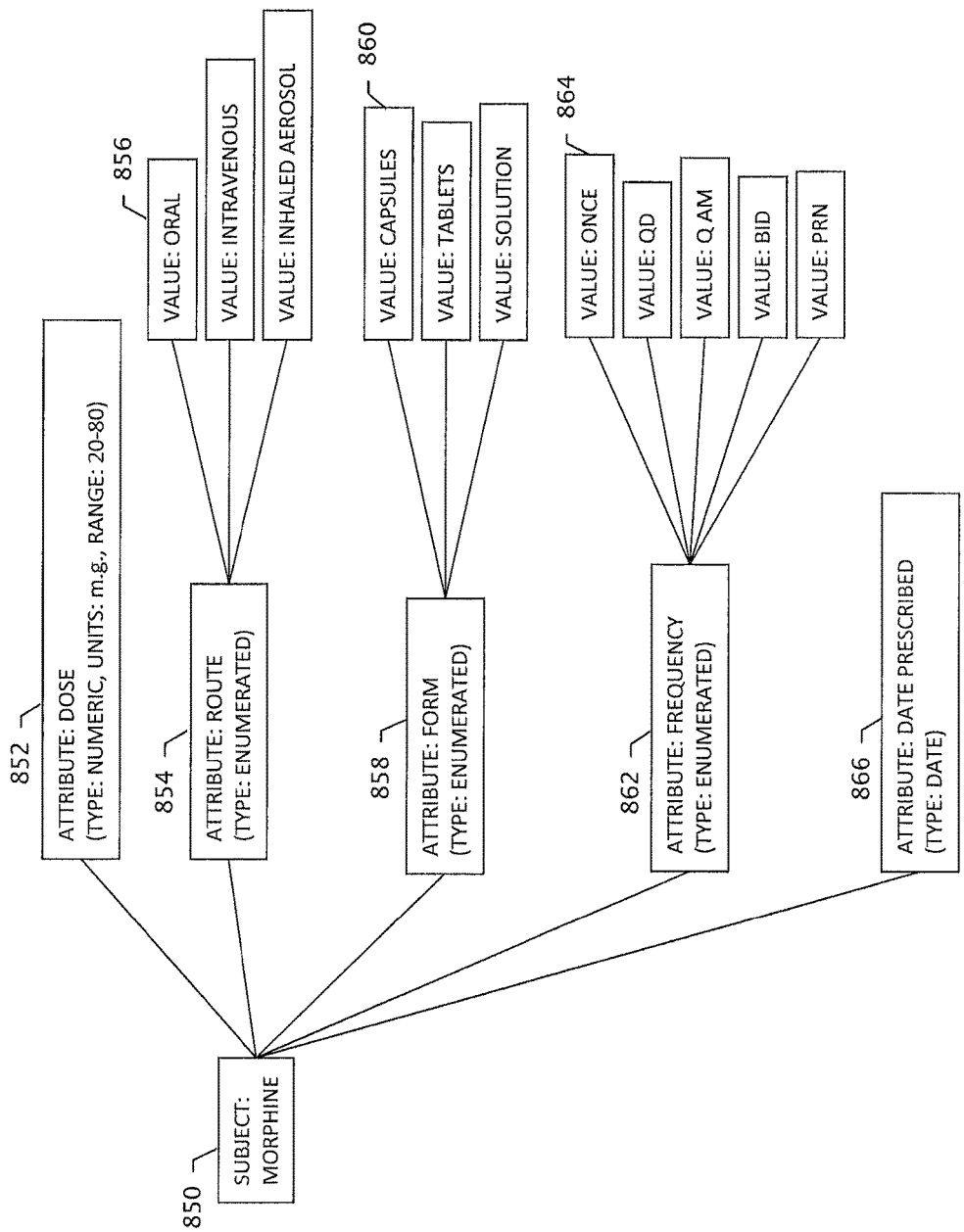
FIG. 4 is a diagram representing the data relationships among the subject, attributes and value in a structured sentence

For greater understanding, reference will now be made to FIG. 4, a diagram illustrating the underlying data structure of a specific example of a structured sentence for an order for a drug. The subject 850 identifies the drug as Morphine. Attributes could include, for example, the dose 852, the route 854, the form 858, the frequency 862, and the date prescribed 866. Other possible attributes, such as the number of refills allowed, the amount of the drug to be dispensed, whether or not the associated prescriptions should be sent to a pharmacy, etc., are not illustrated in FIG. 4. For the route 854, a collection of valid response options 856 could are be provided, including oral, intravenous, inhaled aerosol, intramuscular, topical, etc. For the form 858, valid response options 860 include capsules, tablets or solution. For the frequency 862, valid response options 864 include once, QD (daily), Q AM (once a day in the morning), BID (twice a day), PRN (as needed), etc. Note that, in a preferred embodiment of the system, attributes may take the form of data structures that contain other nested attributes, such that the overall data model for a structured sentence forms a hierarchy of attributes and valid response options. It is also understood that a structured sentence may have attributes where the permitted value is unstructured text, such as a structured sentence for a patient's chief complaint, where an attribute of the structured sentence could contain the complaint in the patient's own words. It is further understood that a structured care plan may contain nodes within the hierarchy of nodes that comprise the structured care plan, that do not have an associated structured sentence. Such nodes without associated structured sentences include nodes that are present to aid in the organization and to facilitate navigation within the care plan, and nodes that the user entered as free text, as described later.

Returning now to FIG. 2, some structured care plans supported by the embodiments are single authorship care plans 270, created and signed by a single clinician user. Other structured care plans supported by the embodiments are multi-authorship care plans, created through collaboration of two or more members of the clinical team involved in the care of a particular patient. The embodiments support open multi-authorship care plans 280, where all clinical team members involved in the care of the patient can participate in the authorship of the care plan, as well as invited authorship care plans 275, where participation is limited to the clinicians that were invited to do so by either the clinician user who initiated the authorship of the care plan or one of the other previously invited authors of the care plan for a particular patient. For single authorship care plans, the embodiments support a point-in-time method 285, where the care plan is signed and finalized at a particular point in time. The embodiments also support a longitudinal method 286, where the care plan is intended to be amended and updated over time. For invited multi-author care plans, the system also supports both points in time 287 and longitudinal 288 care plan models. For open multi-authorship care plans, only a longitudinal care plan method is supported in the preferred embodiment. As described at 295, the Care Planning and Management System is distinguished, among other ways, in its support for diverse types of care plan information, including care plan elements extracted from external systems, and various types of unstructured and structured care plan structures and methods. This support for diverse care plan information anticipates the potentially long transition period within health care organizations seeking to transform to more highly structured and collaborative methods of multi-author, longitudinal care planning, when some clinicians are farther along in that transition, while others continue to use a less structured and less collaborative approach.

Figure 5:
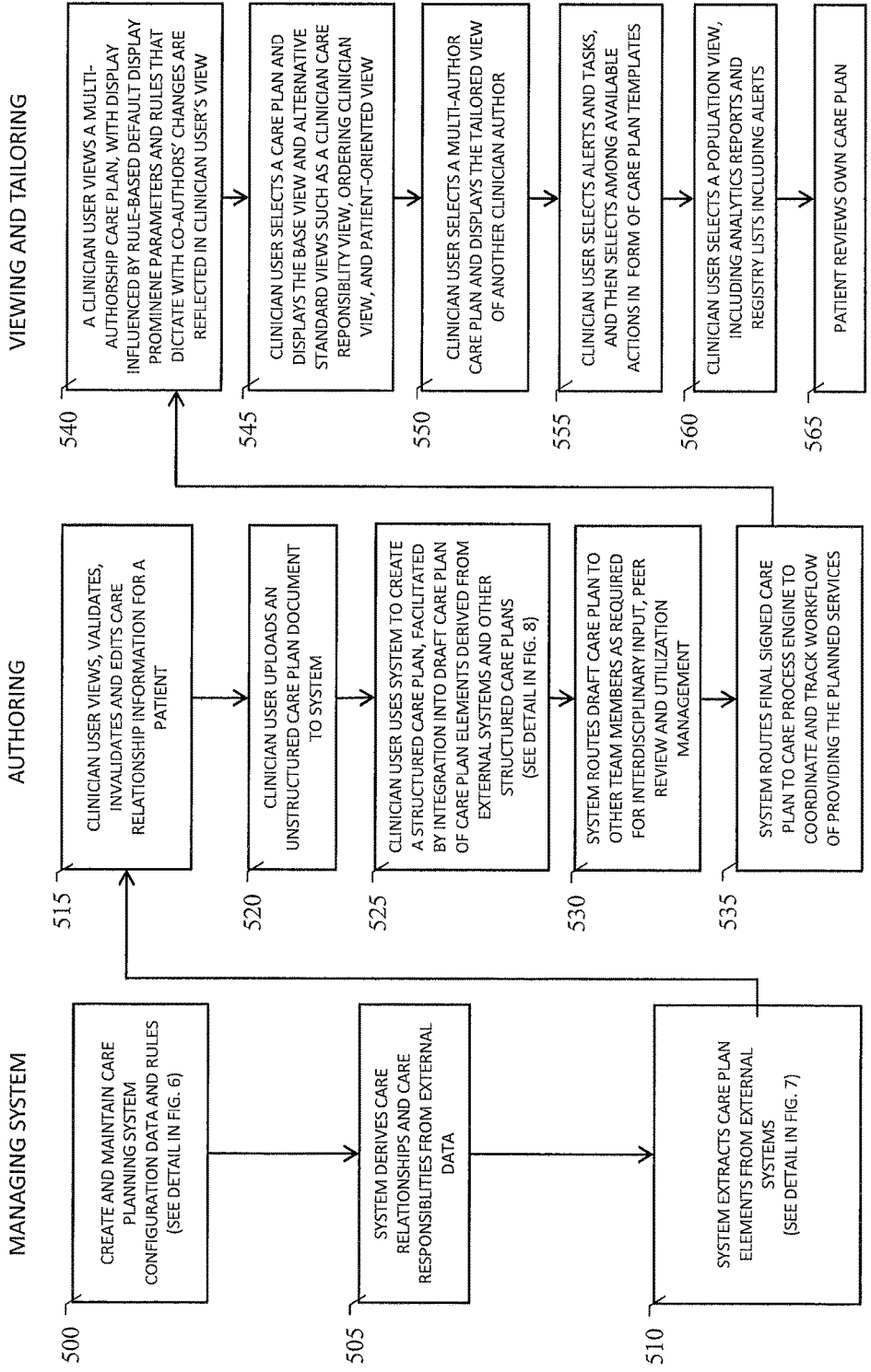
FIG. 5 is a high level process flow diagram of the method for computer-assisted care planning and management

Referring now to FIG. 5, the overall method for care planning and management is illustrated. It should be noted that, although the diagram show a series of linear steps, in actuality, the methods described in the steps are intended to be executed in any convenient order on an ongoing basis by the system and its users. The first step 500 in this method is to create and maintain care planning system configuration data and rules. More detail on this step is provided in FIGS. 6, 11 and 14, described below. Continuing in FIG. 5, the next step 505 is for the system to derive care relationships and care responsibilities from external data.

Figure 9:
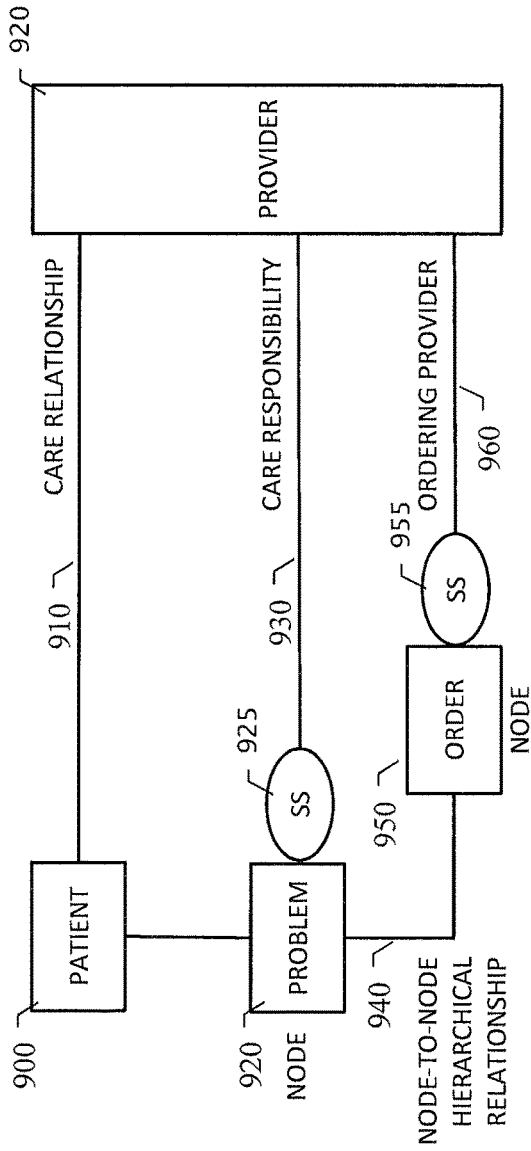
FIG. 9 is a block diagram depicting the high-level information model for structured care plans

Referring to FIG. 9, the diagram provides a high-level information model for structured care plans, with an emphasis on how the health care provider fits into the model. The care plan data structure used for the embodiments identifies a particular patient 900, and associates that patient with any providers that are involved in the care of the patient. Care relationship data 910 represents this basic membership of clinicians in the clinical team caring for the patient. Such care relationship data may be incorporated separately within each structured care plan data structure. Alternatively, in a preferred embodiment of the system, this care relationship data is shared by all structured care for a patient in the system, such that the system maintains a comprehensive single list for all care relationships for each patient, versioned with effective dates and end dates.

The care plan data structure also includes a collection of zero or more problems, represented as problem nodes 920. Care relationship data 930 included in the care plan represents the association of particular patient problems with the providers who have accepted primary responsibility for the patient. In one embodiment of the system, such problem data directly associates the problem node with the provider. In a preferred embodiment, the care responsibility is represented as an association to a structured sentence 925, labeled "SS." Specifically, a structured sentence for problems can include an attribute for the particular provider who has care responsibility for the particular problem for the particular patient during a particular time period specified with an effective data and an end date. This explicit representation of the care responsibilities in the structured care plans supported by the embodiments is important for the simple reason that clear, unambiguous assignment of responsibility can be helpful to reduce the risk of duplication of effort or gaps in care could result due to confusion among the clinical team members about which clinician is handling which patient problems.

In addition to including care plan nodes for medical problems 920, the structured care plans in the embodiments include other types of care plan nodes, such as order nodes 950, goal nodes, barrier nodes, status nodes, outcomes nodes and other types of nodes as may be specified in system configuration data to be described below. Such nodes within the structured care plans are associated explicitly in the form of node-to-node hierarchical relationships 940. Orders include an identifier of the clinician who made the clinical decision to make the order. This association is represented in the diagram as ordering provider 960. The ordering provider is declared when the order is added to the care plan.

Care relationships 910 and care responsibilities 930 can be declared by the clinician, such as when the clinician user is creating or editing a structured care plan, or when the clinician user is editing the overall list of the patient's care relationships in the preferred embodiment of the system described above. Returning to FIG. 5, the system can alternatively derive care relationships and care responsibilities from external data 505. For example, the system can extract data regarding care delivered by a clinician to a patient from claims data, and apply rules to attribute the patient to the provider, such as by deriving a care relationship if the encounters of a patient with the provider represented the plurality of all encounters of the same type by the patient with all providers during at specified time interval. The system accomplished care relationship and care responsibility derivation based on rules that can be amended and improved over time so as to achieve a balance between sensitivity to detect care relationship and care responsibilities that exist and the specificity to avoid falsely asserting care relationships and care responsibilities that do not exist.

Both declared and derived care relationships and care responsibilities are assigned types, such a primary care relationship, a specialist consultant care relationship, or a nurse care management care relationship.

Figure 7:
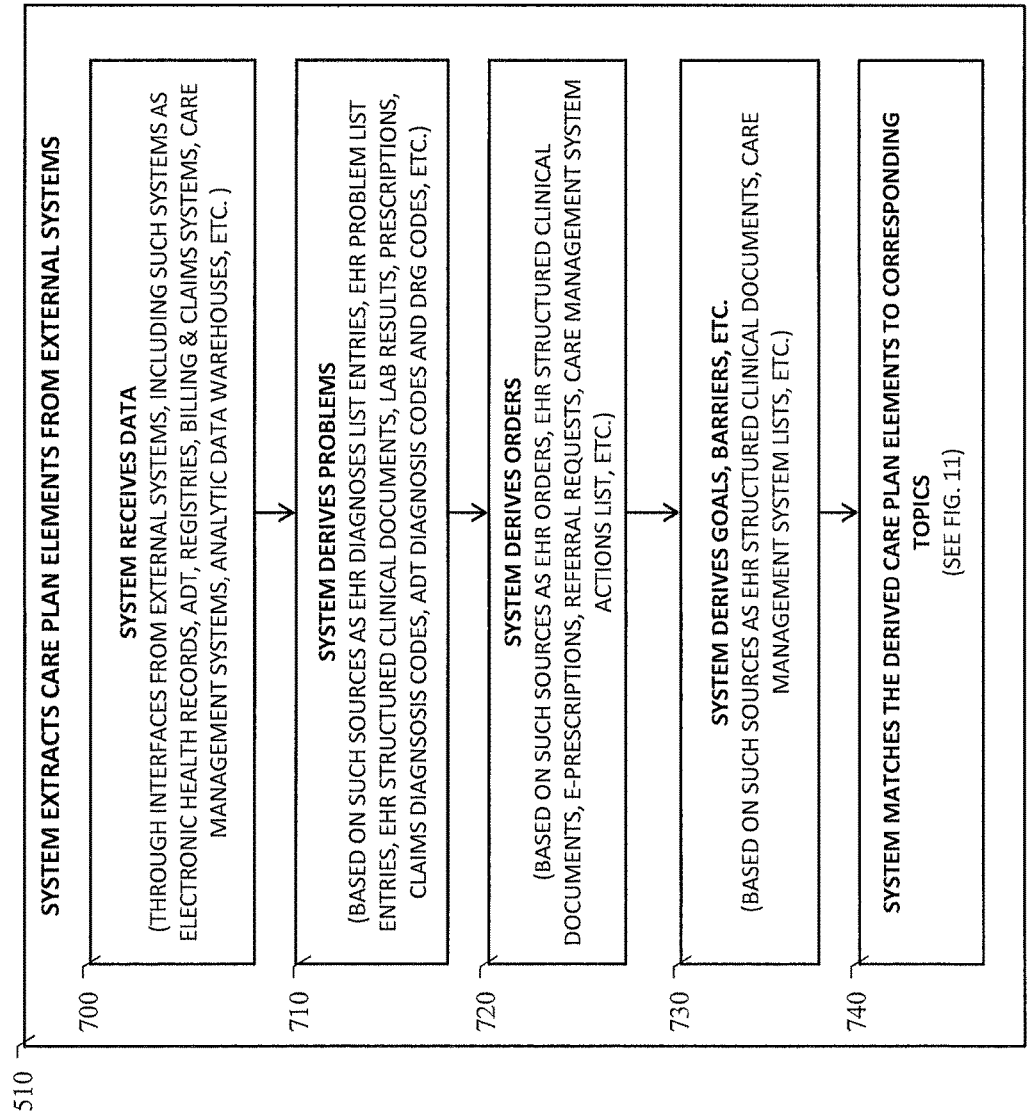
FIG. 7 is a process flow diagram showing the steps for system to extract and derive care plan elements from external systems

The next step 510 is to extract care plan elements from external systems. Turning to FIG. 7, the system received data 700 through interfaces from various external systems such as electronic health records, admit-discharge-transfer (ADT) systems, registry systems, billing and claims processing systems, care management systems, and analytic data warehouses. The system then uses this data to derive problems 710, orders 720, goals 730, barriers, and possibly other types of care plan nodes. In step 740, the system then uses a matching algorithm to map these derived care plan elements to corresponding topics in a hierarchical catalog of available topics.

Figure 11:
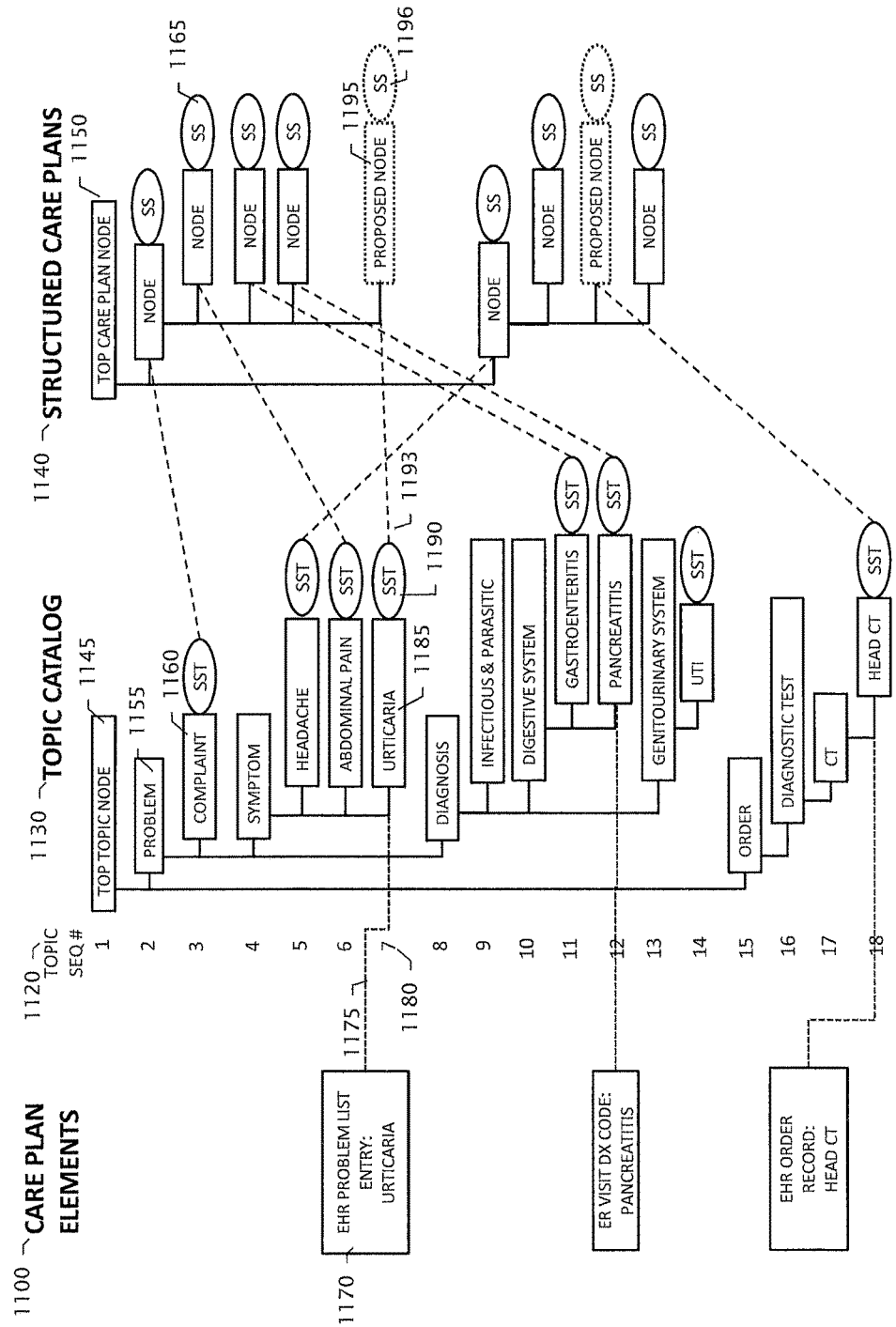
FIG. 11 is a block diagram depicting the relationships among topics, structured sentence templates, care plan nodes, structured sentences, and care plan elements

Refer now to FIG. 11, a diagram that illustrates the relationships among important data constructs used for the system. The diagram includes examples of care plan elements 1100, including the example 1170 of the medical symptom of urticaria (itchy skin) extracted from a problem list of an external electronic health record system. In the center of the diagram is a hierarchical catalog of topics 1130, beginning with a top topic node 1145. This hierarchical structure represents a catalog of the care plan elements and the corresponding nodes that can be incorporated into care plans. The topics include such high level concepts as "problem" 1155, with more specific sub-types of problems such as complaint 1160 represented as child topics under the problem topic. Since the topics are organized in a hierarchy, with each of the sibling nodes at each level of the hierarchy placed in a particular order, the entire tree of topics can be assigned of topic sequence number 1120. Since the topic catalog represents the available structured elements that can be added as nodes to a care plan, and since it has a strict sequence and hierarchy, the topic catalog can be used to assign a default position to a node when it is added to a structured care plan, assuring that structured care plan nodes have a starting default configuration that groups like topics together and presents care plan nodes in a clinically meaningful and intuitive manner. The diagram also illustrates the edge 1175 (line) connecting the urticaria care plan element extracted from a problem list in an external system to the corresponding topic tree node for urticaria. This edge represents the mapping of the care plan element to the topics accomplished in step 740 (FIG. 7).

Returning to FIG. 5, the next step 515 involves a clinician user viewing and editing the care relationship information that was either derived by the system in earlier step 505, or entered by clinician users in earlier instances of executing steps 515 and 525. This step 515 is applicable to the preferred embodiment of the system, where care relationship information is maintained in a data structure that is shared by any and all structured care plans that have been created for a patient. In the alternative embodiment where care relationship information is separately maintained within the data structure of each structured care plan, then this validation, invalidation and editing step would only be accomplished as part of the steps involving creation and editing of particular structured care plans.

In the next step, 520, the clinician user uploads an unstructured care plan document to the system, anticipating and supporting the interim phase in a health care organization's transition to more structured and collaborative approach to care planning and management, when some clinician users involved in the care of the patients will continue to use conventional methods to develop care plans.

Such unstructured documents are persisted in the system's database component for later retrieval and viewing by clinical team members. Such unstructured document can, in an embodiment, are parsed to extract care plan elements, and the resulting care plan elements are then mapped to topics, as is done for data from external systems as shown at 510 and detailed in FIG. 7.

Continuing in FIG. 5, in the next step 525, the clinician user uses the system to create a structured care plan. Referring back to FIG. 2, this structured care plan created by the clinician user can be of the various types defined under 260, including single authorship point in time care plans 285, single authorship longitudinal care plans 286, invited multi-authorship point in time care plans 287, invited multi-authorship longitudinal care plans 275, and open multi-authorship longitudinal care plans 290. The system is intended to support a fully open, collaborative and patient-centered approach to care planning and management, where every clinician involved in the case, regardless of discipline or specialty, shares authorship of a single open multi-author longitudinal care plan. However, even when another structured care plan for the patient has already been created, a clinician user may choose to create another care plan for the patient, provided she has been granted privileges to do so.

Figure 8:
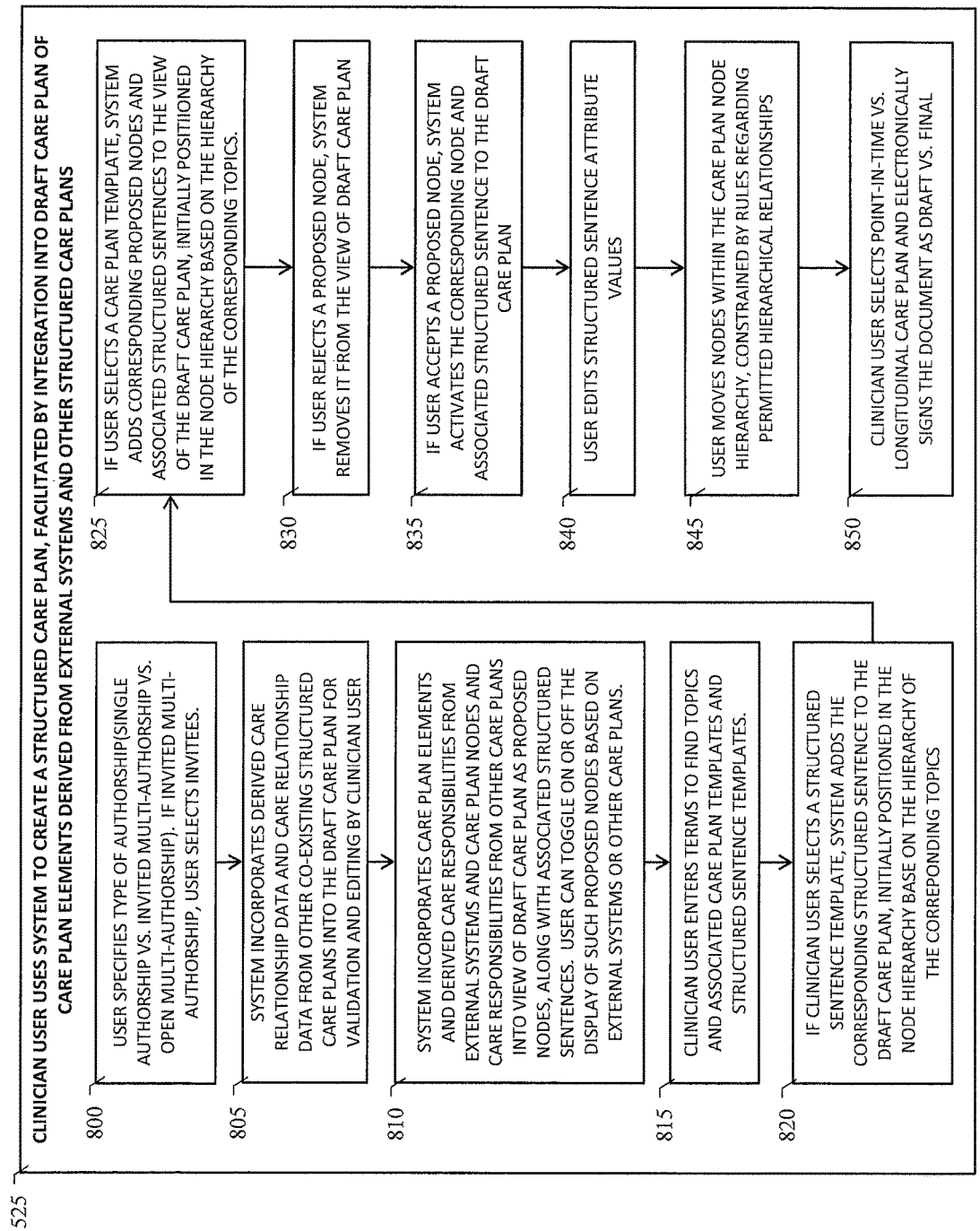
FIG. 8 is a process flow diagram showing the steps for a clinician user to use the system to create a structured care plan

Refer now to FIG. 8, a process flow diagram detailing the method whereby a clinician uses the system to create a structured care plan. It is understood that, although this process flow diagram is shown as a sequence of steps to be accomplished in a linear fashion, it is not limited to the sequence shown, such that the user can interact with the system to accomplish these steps in an order that is most convenient, returning to some steps multiple times and skipping other steps not found by the clinician user to be necessary in the creation of a particular care plan. In the first step 800, the user specifies the type of authorship intended, choosing amongst single-authorship, invited multi-authorship, and open multi-authorship. If the user chooses invited multi-authorship, then the user specifies one or more other clinician users of the system to be co-authors of this structured care plan.

The second step 805 applies to the embodiment of the system, where care relationship information is maintained separately within each structured care plan. In such an embodiment, the system incorporates derived care relationship data and care relationship data from other coexisting structured care plans into the view of the draft care plan, and the clinician user reviews this information, accepting it or rejecting it for inclusion into the draft care plan, thereby reducing data entry burden and reducing inconsistencies across different sources of care relationship information. Such data entry burden and inconsistencies are further reduced in the preferred embodiment, where care relationship information is shared across all structured care plans for a patient.

In the next step 810, the system incorporates into the draft care plan relevant information gleaned from other sources. Care plan elements derived from external systems are incorporated into the view of the draft care plan as proposed nodes with associated structured sentences created from the structured sentence templates that were associated with the topics to which the care plan elements were mapped in a previous step 740 (in FIG. 7).

Referring back to FIG. 11, an example is illustrated. As noted above, a care plan element 1170 for the problem of urticaria was extracted from problem list data obtained through an interface from an external electronic health record (EHR) system, and previously mapped 1175 using a matching algorithm to the urticaria topic 1185 within the topic catalog. That topic entry in the catalog is associated with a structured sentence template 1190 (labeled "SST") having essentially the same data structure as a structured sentence, including a subject and a hierarchical collection of attributes and possible values, along with defaults regarding the inclusion and exclusion of attributes and default values for attributes. When a clinician user uses the system to create a structured care plan 1140, the system incorporates into the view of the draft care plan proposed nodes 1195 corresponding to the topic 1185. The system uses the topic catalog hierarchy and the associated topic sequence number 1180 as a basis for determining the initial location of the proposed node 1195 within the structured care plan hierarchy, assuring that the proposed node is shown along with nodes with related topics in an manner that is clinically intuitive and that displays the node in a way that provides the user with meaningful context. In addition to including the proposed node in the structured care plan, the system also includes an associated structured sentence 1196, which is created using the corresponding structured sentence template 1190 for the urticaria topic. The proposed node and the associated structured sentence, once created within the draft care plan, maintain the association 1193 back to the corresponding topic and structured sentence template, allowing the topic catalog to be used to support care plan editing rules in later steps.

In addition to incorporating proposed nodes gleaned from care plan elements derived from external systems, the system also incorporates proposed nodes gleaned for other coexisting structured care plans for the same patient. Since nodes within care plans maintain the connection back to the corresponding topic in the topic catalog, the system is able to extract nodes from coexisting structured care plans, identify the corresponding topics, then identify any of those topics that are not already incorporated into the draft care plan, and offer proposed nodes and associated structured sentences positioned in a logical place in the node hierarchy of the draft care plan.

In addition to incorporating proposed nodes and associated structured sentences gleaned from other sources, the system is also designed to propose care responsibilities for problem nodes and proposed problem nodes within the care plan. Such proposed care responsibilities can be obtained from the care responsibility data already present within other coexisting structured care plans for the patient, and from care responsibility data derived from external sources based on derivation algorithms executed during a previous step 505 (in FIG. 5).

Furthermore, the system can identify and alert clinician users of conflicts between care responsibility data. For example, if a coexisting structured care plan for the patient asserts that a particular problem entry such as for diabetes is the care responsibility of a primary care doctor, while another structured care plan that also includes diabetes as a problem assert that an endocrinologist is taking care responsibility for the same problem in the same patient. Similarly, a care responsibility derivation algorithm applied to claims data for a patient that had frequent visits to a primary care physician with a diagnosis code for diabetes but not visits to the endocrinologist in the last year, could create a derived care responsibility between the patient and the primary care physician. The system can identify that this derived care responsibility is inconsistent with a structured care plan that asserts a care responsibility for the same diabetes problem to the endocrinologist. Of course, a provider organization that fully embraced a model utilizing only a single open multi-author care plan for each patient would eliminate conflicts across multiple care plans. But, few organizations are likely to be able to accomplish that level of care planning process transformation in the near future. And, even if they did, it is helpful to identify scenarios where the asserted care responsibilities appear to be out of date based on actual encounter data. A key point is that value is added through a number of different capabilities that, taken together, reduce ambiguities of care relationships and care responsibilities, reducing duplication of effort and gaps in care. The system enables the health care equivalent of baseball players calling the ball to avoid the scenario where the ball hits the grass between two players who both thought the other player was going to catch it.

As with other decision support features of clinical information systems, there is a danger of "alert fatigue," where the system offers so many alerts that the clinician users ignore the important alerts mixed in with the less important ones. The system is designed to use configurable rules to drive the derivation of care plan elements and care responsibilities, so as to allow improvements over time to balance between too many and too few proposed nodes and proposed care responsibilities. The system also enables the user to reduce clutter in structured care plans by toggling off and on the display of proposed nodes and proposed care responsibilities.

Continuing with FIG. 8, in the next step 815, the clinician user enters terms to find topics and associated structured sentence templates and care plan templates. A care plan template is a collection of structured sentence templates, together with associated clinical reference information and links and other supportive metadata. A care plan template allows a clinician user to efficiently incorporate a collection of proposed structured sentences into a care plan, without having to go through the effort of finding and selected each structured sentence template or remembering which ones to find in the first place. Care plan templates provide a convenient mechanism for standardizing the care for patient problems, much like order sets in conventional computer-based order entry systems can be used to standardize orders. Care plan templates are created in the system and associated with problem topics in the topic catalog, allowing relevant care plan templates to be conveniently offered to users within the care plan authoring user interface for patients for whom the corresponding problem has been added to their structured care plan. The topic catalog also permits the entry of synonyms and abbreviations for topics, allowing the care plan authoring application to find relevant topics and the associated structured sentence templates and care plan templates using various search terms. Also, the search algorithm leverages the hierarchy of the topic catalog, such that a search term can return templates that are associated with more general ancestor topics or more specific descendant topics.

In the next step 820, if the user selects a structured sentence template, the system adds the corresponding structured sentence template to the draft care plan, not as a proposed node and proposed structured sentence, but as an active node and active structured sentence. As with proposed nodes, the system uses the topic catalog hierarchy and the topic sequence number to initially position the structured sentence within the draft care plan. In a preferred embodiment of the system, the clinician user is able to select whether they want newly added structured sentences to be added to the bottom of the care plan, at the position where they entered the search term, or if they want the newly added structured sentence to move to its logical location based on the topic catalog.

Continuing in FIG. 8, in the next step 825, if the clinician user selects a care plan template, the system adds the corresponding proposed nodes and associated structured sentences to the view of the draft care plan, initially positioned in the node hierarchy of the care plan based on the topic catalog information.

All proposed nodes are displayed in the user interface that makes their status as proposed nodes clear and which offers the user the ability to select and activate it. For example, in a preferred embodiment, proposed nodes and associated proposed structured sentences are displayed in a different color or with different color saturation, and have a unchecked check box to the left. Different embodiments of the system may offer different user interactions for selecting, activating and rejecting proposed nodes. For example a pen-based tablet may offer a cross-out, strike-through or fling-out gesture for rejecting proposed nodes. Also, to facilitate viewing and decision-making about proposed nodes that may be spread out across a potentially large care plan node hierarchy, a preferred embodiment of the system offers the use the ability to toggle to a view where all the proposed nodes are displayed together, with a user interaction offered to permit the user to check or uncheck the proposed nodes all at once in this view. Different views and features of different configurations or embodiments of the system can be optimized to balance between the need to ensure that the clinician user made fully informed clinical decisions, and the need to reduce the burden of using the system on busy clinicians.

Continuing to step 840, the clinician user edits structured sentence attribute values as necessary. In a preferred embodiment of the system, the user interacts with the structured sentence directly, clicking on the textual representation of an attribute value to reveal a list of alternative valid values or a user interface gadget that facilitates entry of more complex attribute values such as dates, times, time ranges, blood pressures, anatomic locations, etc. The preferred embodiment offers the ability to display a terse version of a structured sentence, with a "<more>" affordance to allow toggling to a more verbose, comprehensive display of the attributes that are available for display. In a preferred embodiment of the system, the structured sentences templates allow the entry of validation logic to enforce not only that each field has a valid value, but also that the combination of values within the structured sentence is valid. The preferred embodiment also includes the ability for structured sentence templates within care plan templates to include logic defining whether or not to create a proposed node and an associated proposed structured sentence in the draft structured care plan when the care plan template is selected. This "smart template" capability can be used, for example, to create proposed nodes for services only relevant to adults only in care plans for patients that exceed a threshold age.

Continuing in the process diagram to step 845, the clinician user moves nodes within the care plan hierarchy so as to create a clinician-tailored view of the care plan. The system is designed to strike a balance between offering the clinician enough flexibility to permit her to create a view which reflects her clinical thinking with high fidelity, while constraining flexibility based on rules to ensure that the care plan makes sense and that the movements of nodes by one clinician do not cause a distortion of the meaning intended by another clinicians in a multi-authoring care plan.

Figure 10:
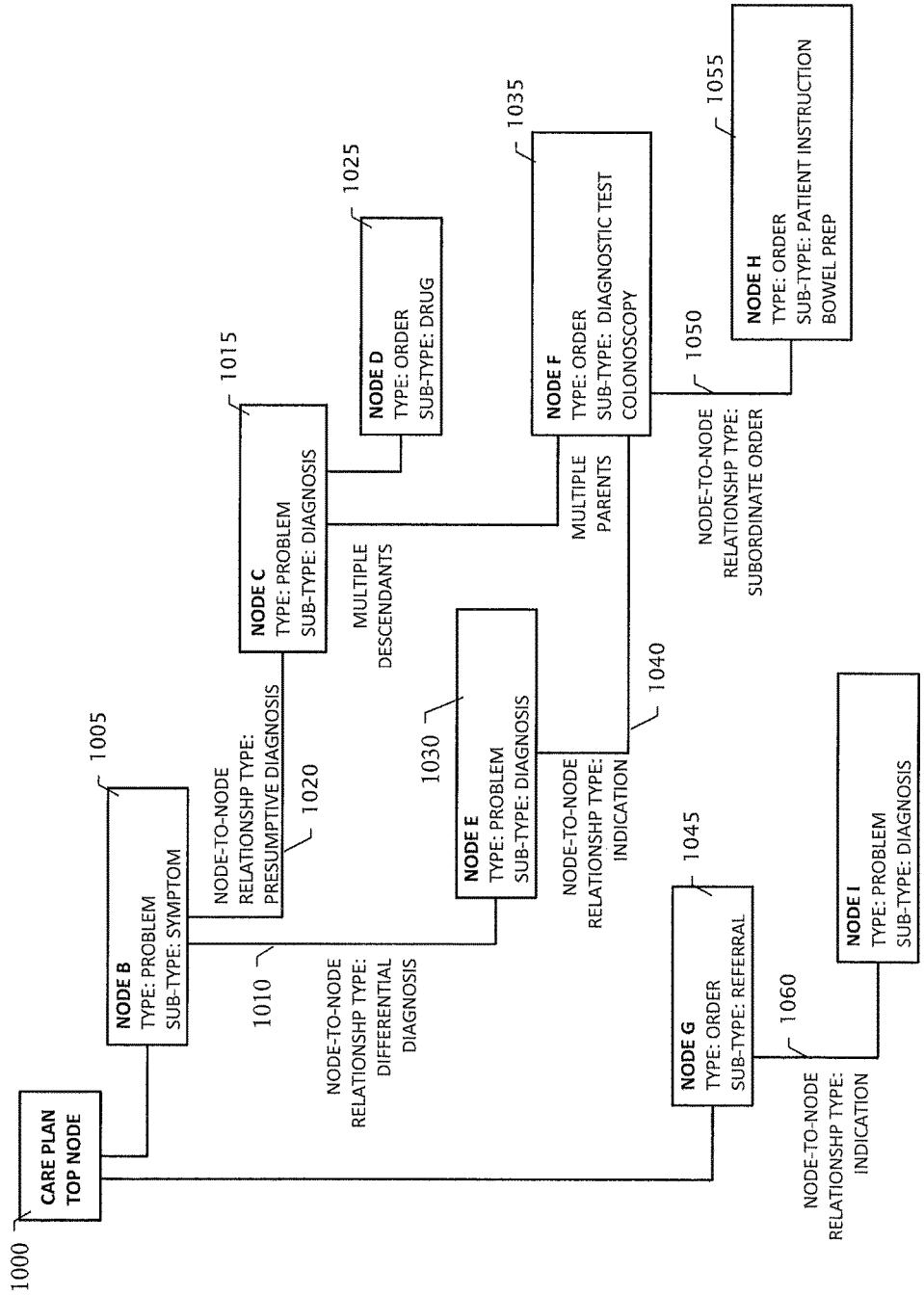
FIG. 10 is a block diagram depicting the node types and sub-types and node-to-node relationships in structured care plans

Referring now to FIG. 10, the diagram provides more detail regarding the data structure used by the system for structured care plans, with an emphasis on node types, node sub-types, and node-to-node relationships. As previously noted, structured care plans in the system use a data structure based on a hierarchy of nodes, connected by edges described as node-to-node relationships. At the top of the hierarchy is a care plan top node 1000. The diagram illustrates that nodes such as 1005 have a type such as problem and a sub-type such as symptom. Node 1005 has two child nodes 1015 and 1030, both being of type problem and both having sub-type diagnosis. But the two nodes are distinguished in that they have different node-to-node relationship types. Node 1030 is associated with its parent node 1005 through a node-to-node relationship 1010 of type "differential diagnosis," meaning that it is merely a diagnosis that is being considered as a possible diagnosis by the clinician. Node 1015 is associated with the same parent node 1005 through a node-to-node relationship 1020 of type "presumptive diagnosis," meaning that is has not been definitively confirmed by diagnostic tests, but is judged to be sufficiently likely to be true as to warrant initiation of therapy while continuing to pursue confirmation through diagnostic testing. Consistent with this distinction between differential and presumptive diagnoses, node 1015 has child order nodes for both therapeutic and diagnostic orders, while node 1030 only has diagnostic orders as children.

Also illustrated in FIG. 10 is the flexibility in the hierarchical relationships between problems and orders. Node 1030 is problem node that has order node 1035 as a child, while node 1045 is an order node that has a problem node as a child. In both cases, the node-to-node relationship type is "indication," meaning that the problem is the reason justifying the order. Also illustrate is the support for orders nested within other orders, such as order node 1035 for a colonoscopy test having a child node that is an order node of sub-type patient instruction for bowel preparation instructions. Such a nesting of orders may not be necessary in an embodiment of the system that includes the use of a workflow automation system to coordinate and track the process of execution of an order such as a colonoscopy order. In that scenario, the patient instructions for the bowel preparation are considered process steps in the process for executing the colonoscopy order. However, the ability of the system to support nesting of orders allows greater flexibility in how provider organizations conceptualize the relationship between higher level orders, and the specific steps by which clinical team members in different disciplines care them out and coordinate them over time. Lastly, the diagram in FIG. 10 illustrates that, in a preferred embodiment, the system supports the ability of a child node such as a node for a diagnostic test 1035 to be simultaneously associated with multiple parent nodes, such as two different diagnoses 1030 and 1015 that could be confirmed or rejected based on the results of the test. In such a preferred embodiment, the user interface for displaying structured care plans would include the same node in multiple places in the hierarchy. Such as user interface design would include clear visual indications of the existence of the multiple parent relationships, such as by highlighting both places the node is displayed whenever the user selects the node from either location, so as to avoid the clinician user inadvertently making a change or deletion without realizing the full context of the change.

Figure 12:
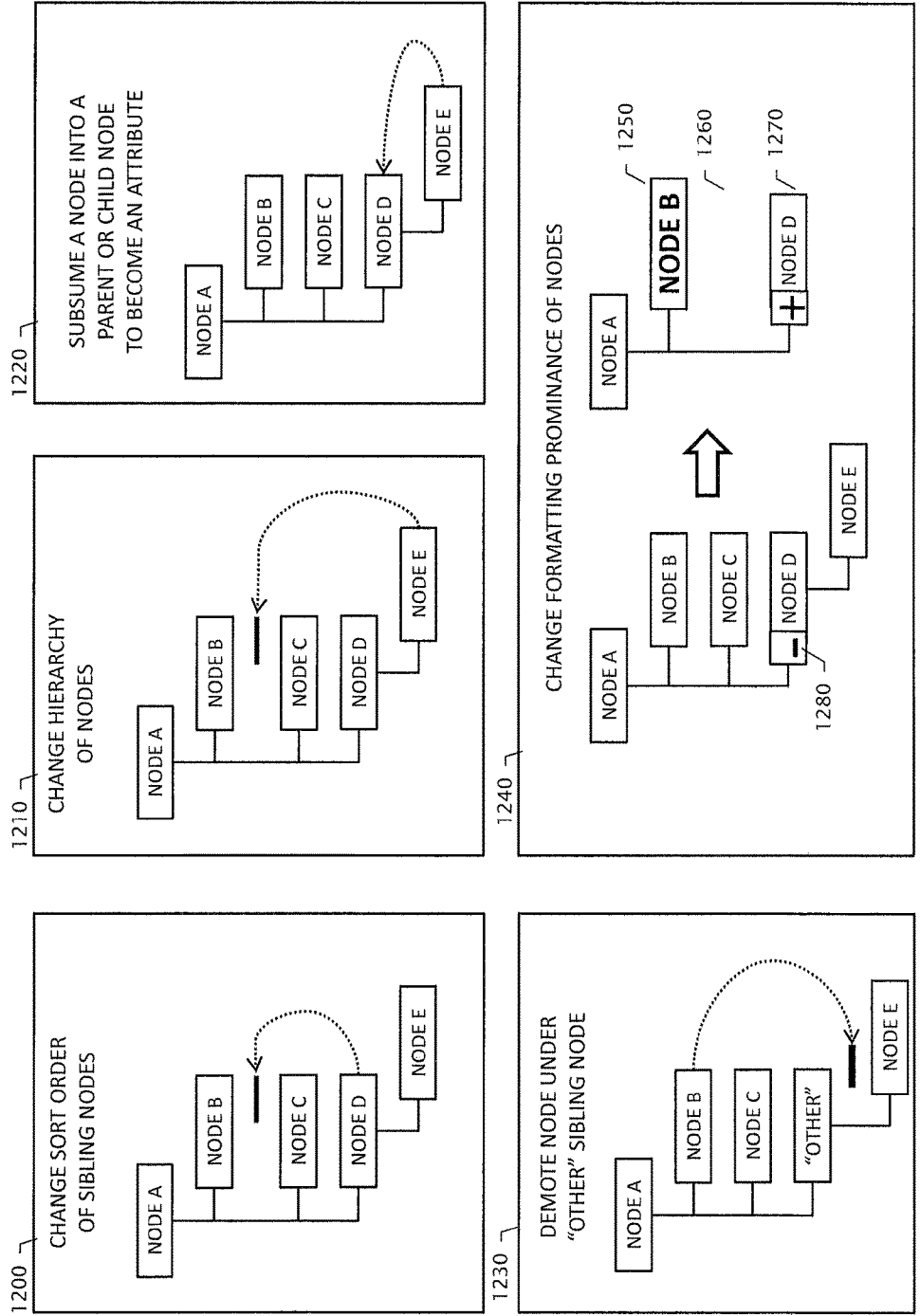
FIG. 12 is a block diagram illustrating five types of care plan tailoring, including moving care plan nodes to permitted positions with the node hierarchy and changing display prominence of nodes in structured care plans

Turn now to FIG. 12, a diagram explaining the types of permitted movements of care plan nodes within the node hierarchy of a structured care plan by a clinician user who is using the system to create or edit such a care plan. As shown in 1200, the clinician user can use the system to change the sort order of sibling nodes within the node hierarchy of a structured care plan, such as moving the node D to a location between sibling nodes B and C. In this example, node E, a child of node D, would remain as a child of node D, being displayed in the hierarchy just above node C. As shown in 1210, the clinician user can also use the system to change the hierarchy of nodes, such as by moving node E to a position between node B and node C, promoting it up one level of the hierarchy. As shown in 1220, a clinician user can also use the system to move a node onto its parent or child node, such as moving node E on top of its parent node D, causing the structured sentence associated with node D to be subsumed to be displayed as if it was an attribute within the structured sentence associated with node D, and causing node E to be not separately displayed in the view of the structured care plan. In a preferred embodiment of the system, such a subsumption move does not remove the moved node or its associated structured sentence from the underlying node hierarchy, but merely causes a change in the display of the moved node and the node into which it is subsumed. Note that these three types of changes to the relationship between the nodes of a structured care plans are restricted to permitted positions based on rules and associated rule data, as described later.

As shown in 1230, the clinician user can also use the system to "demote" a node so that it is not displayed at the same level within the view of the structured care plan, but is instead displayed under a display node named "other" which appears at the same level the node have been at within the structured care plan node hierarchy. As with the preferred embodiment of the node subsumption move, the move to demote a node in this way does not actually change the underlying node hierarchy, but merely causes a change in the way the node is displayed in the view of the care plan so as to make it less prominent. Finally, as shown at 1240, the clinician user can change attributes of structured care plan nodes so as to cause them to be displayed with greater or lesser prominence. For example, as shown at 1250 and 1260, a node can be made more or less prominent by changing font size, font boldness (emphasis), font color, or font color saturation. In addition, the user interface of the system supports opening and closing the hierarchy at levels of the tree. As shown at 1280, a preferred embodiment of the system includes a plus and minus affordance (symbol), or other equivalent symbol such as triangles pointing to the right or pointing toward the lower right, to allow the user to toggle between a view where the descendent nodes are displayed and a view where the descendent nodes are not displayed.

Figure 13:
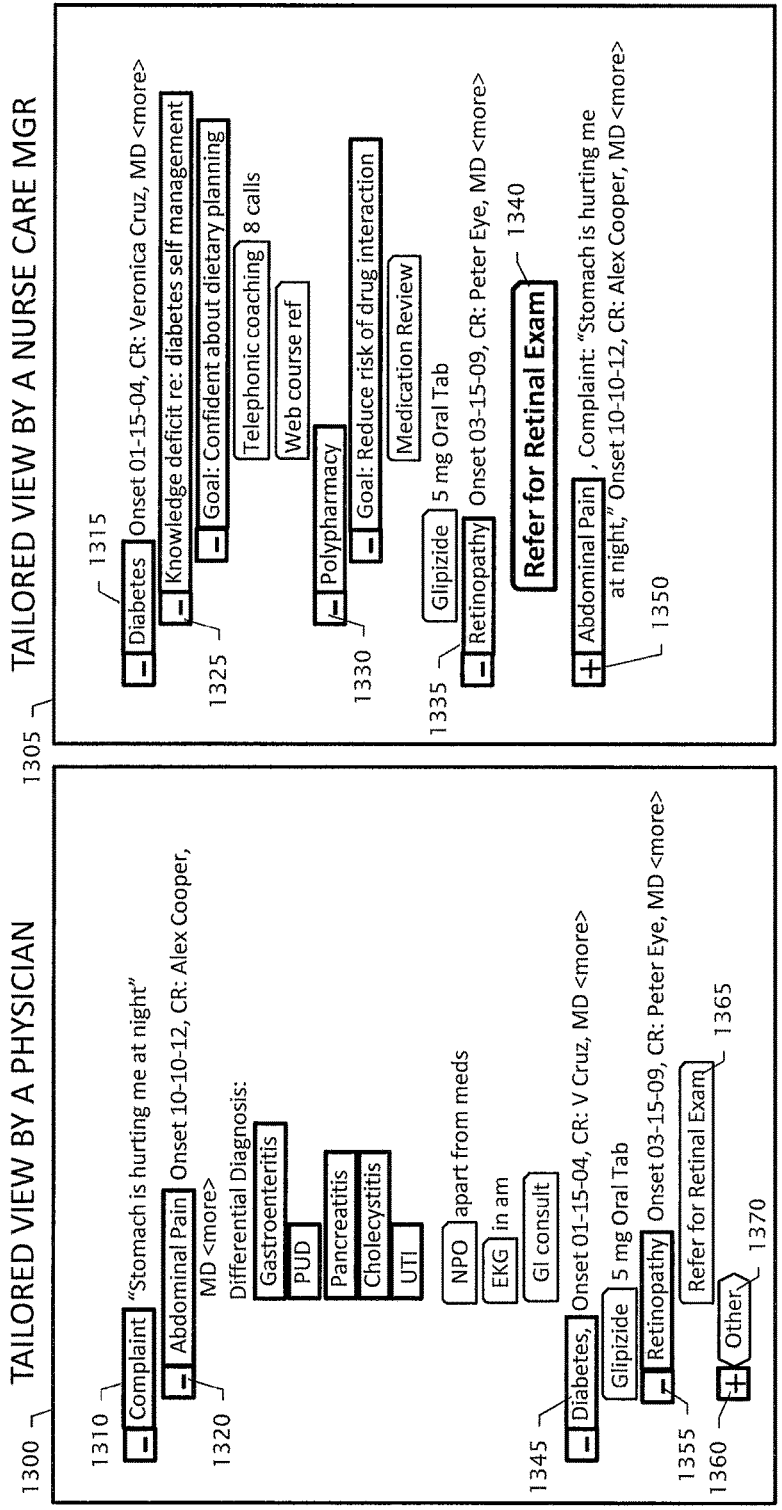
FIG. 13 is a diagram illustrating how two different clinician users may create different tailored views for the same multi-author care plan

Turning now to FIG. 13, a diagram is provided an example showing how different clinician users can use these permitted changes to the underlying hierarchy of nodes and to the node parameters that drive display characteristics of nodes to create very different clinician-tailored views for the same multi-author structured care plan for the same patient. The diagram compares a clinician-tailor view created by a physician user 1300 to one that might be created for the same patient by a nurse care manager 1305. The care manager's view shows the diabetes node 1315 sorted in the first position within first layer of the hierarchy below the top node, while the physician's view shows the diabetes node 1345 sorted in the second position within the first layer of the hierarchy below the top node, thereby illustrating the ability to use the system to change the sort order of sibling nodes. The physician's view shows the retinopathy problem node 1355 as a child node under the diabetes problem node 1345, while the care manager's view shows the retinopathy node 1335 as a sibling of the diabetes node 1315 at the first level of the hierarchy below the top node, thereby illustrating the ability to use the system to change the hierarchy of the underlying nodes. The physician's view shows the complaint problem node 1310 as a parent to the abdominal pain symptom problem node 1320, while the care manager's view shows the complaint node's structured sentence attributes, including the patient's quote "stomach is hurting me at night" displayed as if it were an attribute of the structured sentence associated with the abdominal pain symptom problem node 1350. This illustrates the ability of the system to be used to change the display to subsume a parent node within a child node. The care manager's view shows problems for knowledge deficit 1325 and polypharmacy 1330 as child nodes of the diabetes problem node 1315, while the physician's view shows that the physician demoted those two problems to be displayed under a "other" display node 1370, and then used the user interface control 1360 to hide display of the demoted nodes. The physician's view shows the display of all the descendant nodes under the abdominal pain problem node 1320, while the care manager's view shows the "plus" symbol 1350, indicating that there are undisplayed descendant nodes. The physician's view shows the order node for referral for retinal exam 1365 displayed in a font of normal size and boldness, while the care manager's view shows the same order 1340 in a font of more prominent size and boldness, illustrating the ability of the system to be used to change display prominence of nodes and associated structured sentences within structured care plans. In short, this example illustrates how a small number of permitted changes to node hierarchy and display prominence can achieve an dramatic difference is the way the same multi-author care plans can be displayed to tailor the structure and display of the care plan to reflect the clinical thinking and focus of the different members of the clinical team. Note that these permitted changes to the underlying hierarchy of nodes and to the node parameters that drive display characteristics of nodes are not intended to represent an exhaustive list of all permitted manipulations that can allow a clinician user to tailor the view of the care plan to reflect their clinical reasoning and focus. Rather, these are intended to illustrate the types of manipulations necessary for the embodiments to accomplish the necessary balance between the competing goals of consistency and flexibility.

Returning now back to FIG. 8, in the next step 850, the clinician user selects whether she wants the care plan to be created as a point-in-time or a longitudinal care plan. The clinician user then specifies whether she considers the draft to be in draft or final form before applying her electronic signature to save the information to the database. In a preferred embodiment, the system periodically saves the information to the database and allows the user to save the information in an unsigned form to permit the user to resume work at a later point without losing or reentering information. Such unsigned information is available only for resumption by the same user, and is not accessible to other clinician users.

Returning back to FIG. 5, we have now completed the explanation of the step 525 in which the clinician user creates a structured care plan. Moving on to step 530, the system routes a signed care plan for multi-disciplinary input and or workflow enactment, as needed. The system supports two approaches to efficiently achieving multi-disciplinary input. In the first model, consistent with the technology disclosed in U.S. Pat. Nos. 7,020,618 and 7,707,057, the system invokes a workflow process to route the entire draft care plan to appropriate team members for input. In the second mode, rules specified as part of system configuration are used to determine if there is a requirement for review and electronic co-signature by authorized other clinician users before particular types of orders nodes can be activated in the care plan, or before certain other changes are allowed to be signed. Such an approach is intended to be used to provide a means for efficient and flexible teamwork and oversight among members of the clinical team involved in the direct care of the patient as well as extended team members that oversee clinical quality and appropriateness of care. Such an approach can be applied to the oversight of attending physicians over medical students and residents, to the oversight of physicians over allied health professionals, and to the oversight of clinical department and section leaders over the members of their organization. This method can also be applied to peer review and quality management remediation processes, and for utilization management and associated clinical review to assess appropriateness of care and medical necessity and to support decision-making regarding requested prior-authorizations for health insurance payments.

Continuing to step 535, once the plan is signed and any necessary interdisciplinary input is obtained and considered, and any required co-signatures are obtained, the system utilizes its care process engine component, based on workflow automation technology, to instantiate workflow processes and proceed to coordinate and track the execution of each workflow process instance for the patient.

Figure 17:
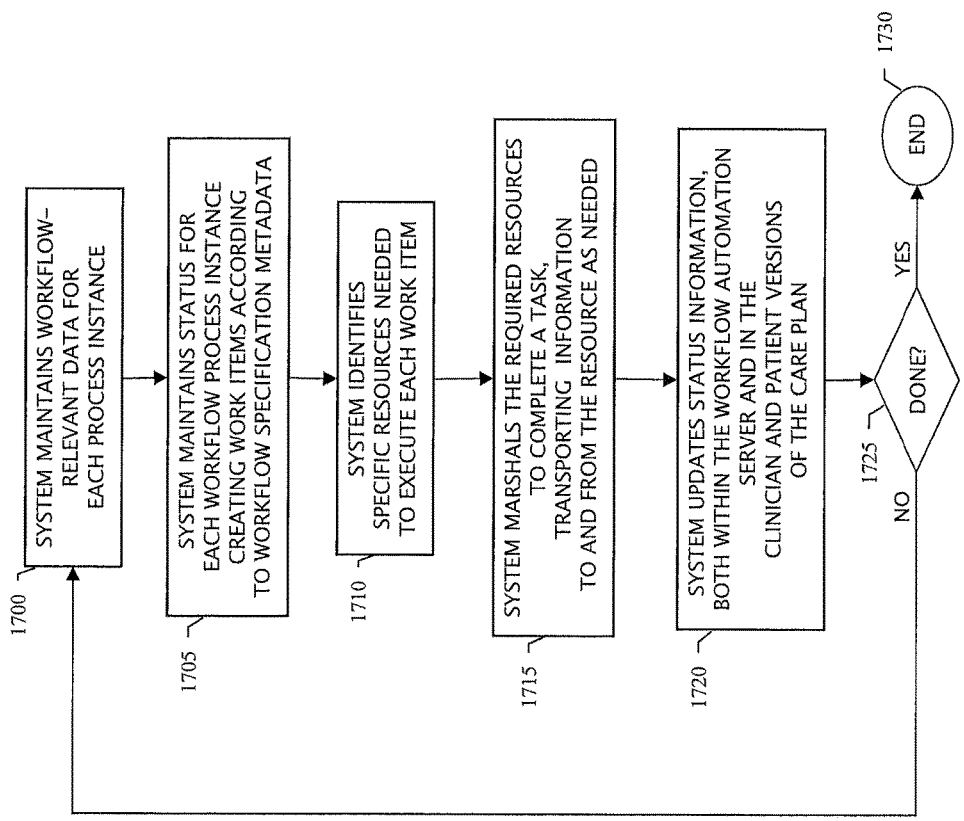

Referring to FIG. 17, a process flow diagram is provided to explain in greater detail the method for instantiating workflows within this care process engine. This aspect of the method of is also described in greater detail in U.S. Pat. Nos. 7,020,618 and 7,707,057.

Returning to FIG. 5, we now turn to the viewing and tailoring of care plan information. In steps 540, 545 and 550, the clinician user views care plan information for patients using alternative available views. To illustrate this, we turn now to FIG. 15, providing a diagram to illustrate the user navigation pathways within the care planning and management system and to external, front-line clinical information systems such as electronic health records systems and registries. The system provides a clinician login 1505, capturing and verifying user credentials to ensure health information remains secure. Clinician users land on a clinical home page 1515 optimized for patient care. Through this home page, clinicians can select patients by entering patient identifying information or selecting from patients scheduled for encounters. Selecting a patient establishes patient context 1535, and displays by default any structured care plan in which the clinician user is an author. By default, a structured care plan is displayed in its "base view," the view that was established when the care plan was authored, showing the natural hierarchy of nodes and associated structured sentences, along the any changes due to a number of factors. The first of these factors is any care plan tailoring that has been previously entered by the clinician user, such as (1) changing the sort order of siblings, (2) changing node hierarchy, (3) subsuming nodes in other nodes, (4) demoting nodes under an "other" node, or (5) changing the formatting parameters for specific nodes and associated structured sentences in the care plan. These five types of tailoring changes have been previously described in detail in the context of FIGS. 12 and 13.

The second factor that influences the base view of a structured care plan presented to a clinician user is rules that have been previously entered by the user regarding default prominence of nodes. In order to reduce the effort required by clinician users to constantly tailor each structured care plan they use, the system permits the entry of formatting rules that apply, be default, subsumption, demotion and the setting of prominence formatting parameters for structured care plan nodes and the associated structured sentences. Such rules can apply the specified tailoring changes based on the care plan node being associated with a specific node in the catalog or one of its descendants. For example, the system permits a user to specify a rule to reduce or increase the prominence of all nodes that are under the "knowledge deficit" topic in the topic catalog hierarchy. Such rules and also be based on the characteristics of the co-author that added the node to the care plan, such as the professional discipline, user role, care relationship type or setting of care of the co-author. For example, a clinician user may specify rules to reduce or increase the default display prominence parameters for nodes added by acute care nurses or care managers or cardiologists.

The third factor influencing the display of structured care plan nodes and the associated structured sentences are rules that determine whether clinician-specific tailoring that may have been done by co-authors is reflected in a clinician user's own view of a structured care plan. Such rules are based on care relationship and care responsibility data. For example, the system can be configured to allow co-authors' tailoring of a care plan to be propagated into a clinician user's own view of a structured care plan if either (1) the co-author was the primary clinician for the patient based on care relationship data or (2) the co-author made the change to a problem node or a descendent of a problem node for which the co-author had accepted care responsibility. The basic premise of such rules is that changes made by the clinician that "owns" the problem or the patient are important to see, while changes by others are relatively more likely to represent "noise."

Figure 15:
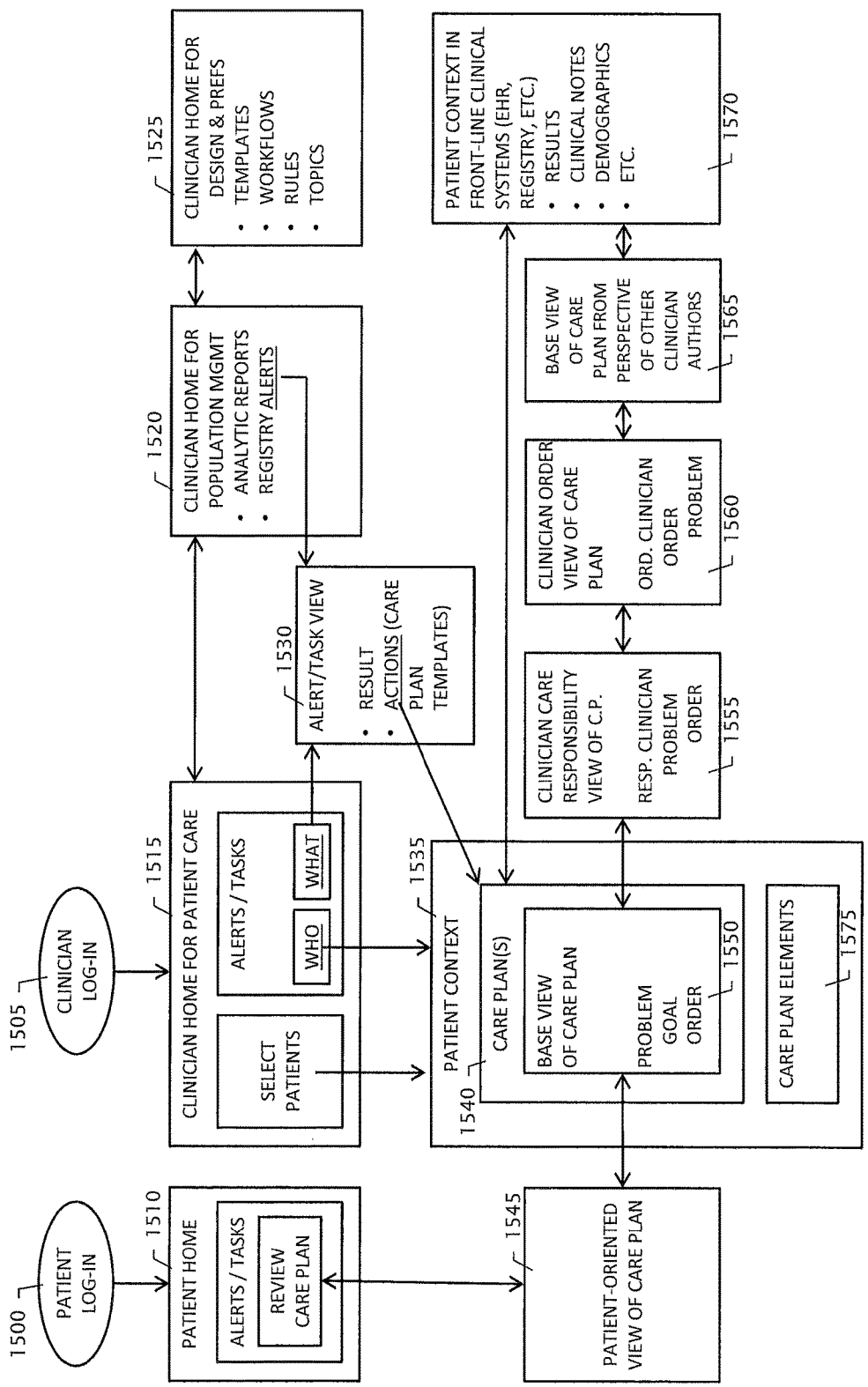
FIG. 15 is a block diagram showing user navigation pathways within the system and to external front line clinical systems

Continuing in FIG. 15, in addition to the base view of the structured care plan 1550, the clinician user may switch to alternative views of the structured care plan, including a view that is organized based on care responsibilities 1555, with the top of the display hierarchy being the various clinicians that have accepted care responsibility for any problems in the care plan, with the next level of the display hierarchy listing problems for which the clinician has taken responsibility, and with the orders and other descendent nodes for the problem displayed below the problems. Also available in this preferred embodiment is a view organized based on ordering physicians 1560, with the top of the display hierarchy listing any clinician user listed as ordering physician for any orders in the care plan, with the next level of the display hierarchy listing the orders ordered by that clinician, with the problems and other nodes associated with those orders presented below the order.

The system also offers the base view of the care plan, shown from the perspective of other clinician authors 1565, as was previously discussed in the context comparing an illustrative example of a physician's view and a care manager's very different views of the same multi-authorship care plan (FIG. 13). Such views allow users to benefit from the seeing how their colleagues conceptualize the same case, and what their colleagues are focusing on. System configuration parameters determine which users and user roles have access to this feature.

The system also allows the physician to view a patient-oriented view of the care plan 1545, allowing the clinician to see the care plan as it is presented to patients to inform their counseling of the patient. The system also allows the clinician user to navigate directly from the patient context within the care planning and management system to pages that offer patient context within front-line clinical systems such as electronic health record systems and registry systems, allowing the user to view lab results, clinical notes, demographic information and other information without having to reenter user credentials or patient identifiers.

Returning back to FIG. 5, we continue to the next step 555, including the clinician user selects alerts and tasks, and then selects among a set of relevant follow-up actions. To illustrate, we return again to FIG. 15. From the clinical home page 1515, the user is presented with a list of alerts or tasks that relate to patients. Selecting the patient within such alerts calls up the patient context page 1535 for that patient. Opening the alert leads to an alert/task view 1530 which displays the message payload of the alert or task, such as by presenting a lab result that is ready for review. The alert/task view also includes links to various actions that are appropriate based on the nature of the alert. These actions take the form of care plan templates. Selecting such a care plan template leads to the care plan view 1540 within the patient context 1535, with the care plan displayed with proposed nodes added to the view of the care plan based on the care plan templates. This feature helps to make alerts more directly actionable, and allows the closing of the loop between alerts and necessary changes to the care plan to be explicit and measureable. In addition, the use of care plan templates as the linkage between alerts and care plan responses works equally well for asynchronous alerts and for synchronous alerts that are offered as part of the care plan authoring process in the preferred embodiment, Returning to FIG. 5, the next step 560 involves the user selecting a population view, providing access to analytic reports and registry lists, including associated alerts. Now returning to FIG. 15, beginning again from the clinician home page 1515, the clinician user may navigate to an alternate home page optimized for population management 1520, offering relevant analytic reports regarding quality and efficiency of care and opportunities for improvement, as well as patient lists that can be generated based on problems within care plans, outstanding alerts, and other criteria. Clinician users may also select an alternative home page optimized for designing improve care processes and specifying preferences 1525. From this page, authorized clinician user may author or maintain the topic catalog, structured sentence templates, care plan templates, various types of rules, and clinical workflow specifications.

Again toggling back to FIG. 5, the final step in the method of care planning and management is for the patient to get engaged and participate in the online review of changes to their own structured care plans. Returning to FIG. 15, the system also offers a patient log-in 1500, which allows patients secure access to a patient home page that includes, among other things, a listing of alerts and tasks directed at patients. Among such tasks is the review of an update to a patient-oriented view of the plan of care 1545. It is understood that embodiment is not limited by this illustration of the navigation pathways within a preferred embodiment of the care planning and management system. It is provided to clarify how aspects of the embodiment can work together to create a coherent whole solution to achieve the envisioned benefits of improved health care.

Figure 16:
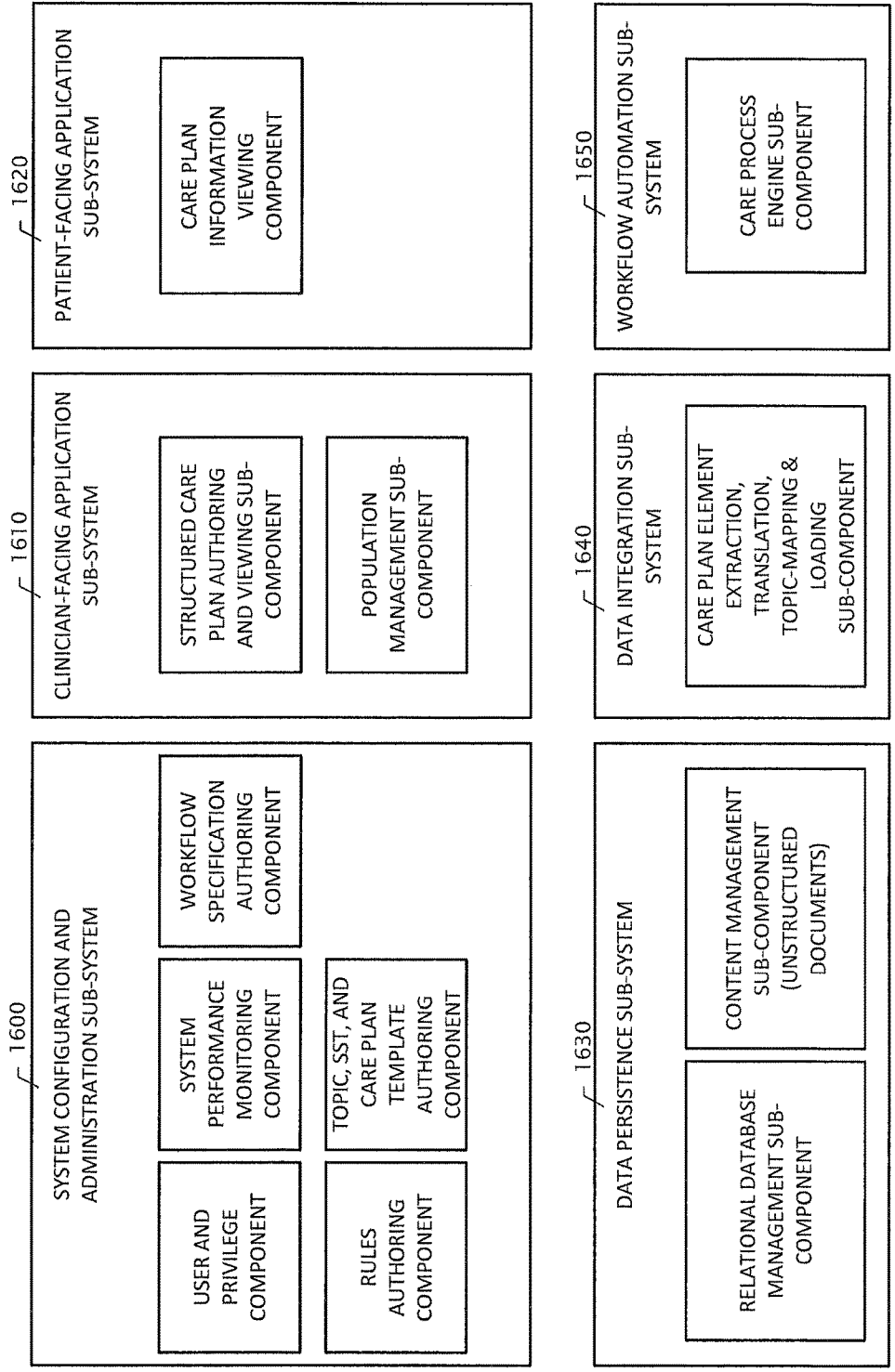
FIG. 16 is a block diagram showing the software subsystems and components of a care planning and management system

Turning to FIG. 16, a diagram is offered to illustrate how aspects of the embodiment can be architected into software components that work together to implement the methods described herein. In this embodiment of the system, software instructions are organized into sub-systems, including subsystems for system configuration and administration 1600, clinical-facing application 1610, patient-facing application 1620, data persistence 1630, data integration 1640 and workflow automation 1650. Each of these sub-systems in comprised of a number of components or modules containing software instructions that address specific aspects of the methods implemented using the sub-system. For example, the system configuration sub-system includes components for user and privilege management, system performance monitoring, workflow specification authoring, rules authoring and authoring of the topic catalog, structure sentence templates, and care plan templates. It is understood that the software instructions necessary to implement the methods could be organized differently into sub-systems and components, and that the diagram illustrating a preferred embodiment is not intended as limiting.

Figure 6:
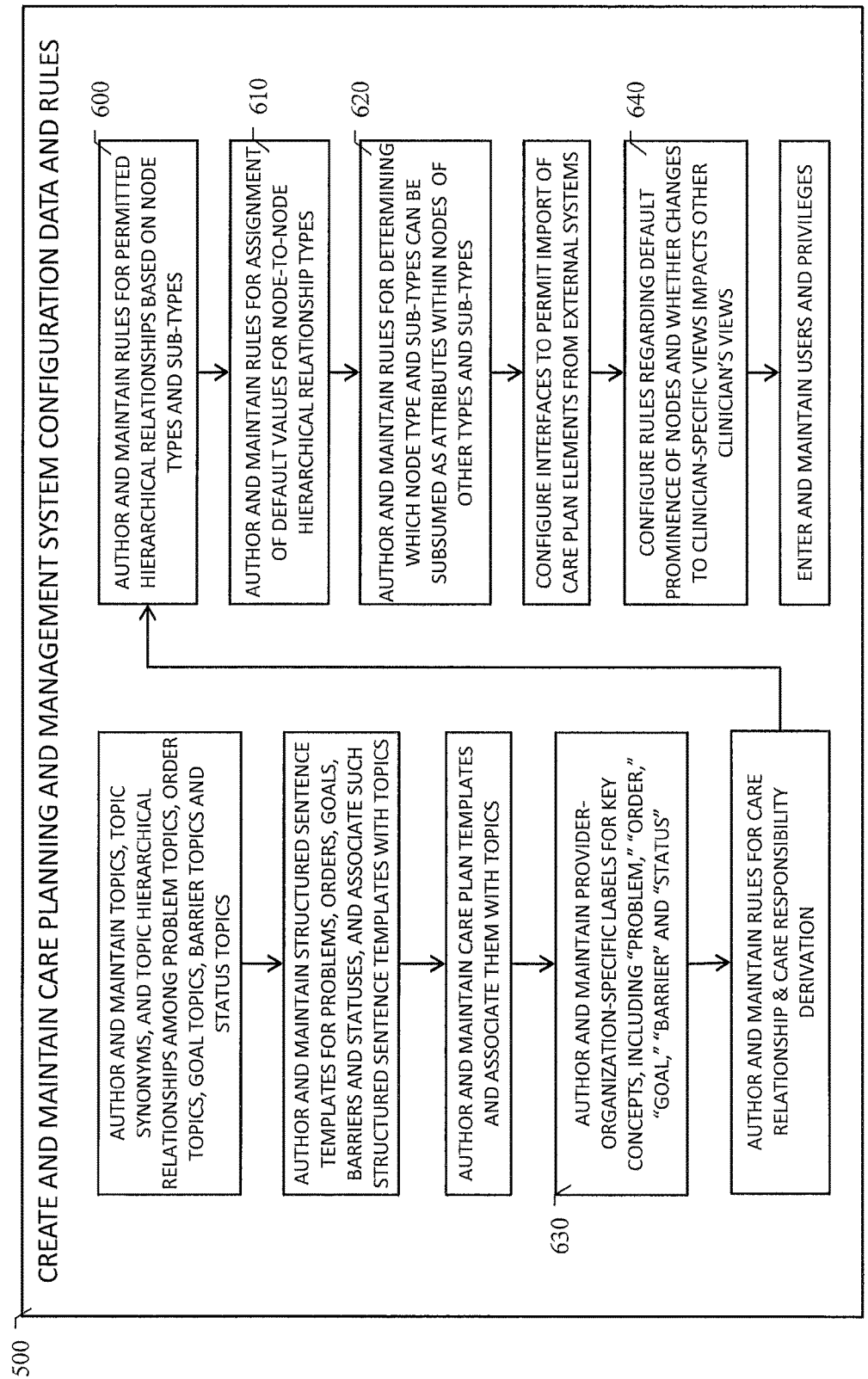
FIG. 6 is a process flow diagram showing the steps to create and maintain care planning and management system configuration data and rules

Referring now to FIG. 6, a process flow diagram is provided to explain in greater detail the method for creating and maintaining the various types of care planning system configuration data and rules. Although the diagram show steps executed in a linear sequence, it is understood that these steps can be done in any order, and the user of the system would frequently repeat each of these steps as part of ongoing maintenance of the system. Many of the steps on shown on this diagram are self-explanatory in light of the previous discussion. However, some steps require further explanation. In step 630, the system maintenance user authors and maintains provider-organization-specific labels for key concepts, including such concepts as "problem," "order," "goal," "barrier," and "status." Efforts to promote interdisciplinary collaboration through multi-author care plans have faced some difficulty due to strong traditions among different disciplines that are reflected in the use of different terminology used in different professional disciplines and in different health care settings to describe similar or overlapping concepts. For example, the terminology of "orders" and "problems" tends to imply use by physicians, while nursing professionals typically prefers different terminology. Rather than "orders," members of the nursing profession may prefer terms such as "actions," "interventions," or "services." Rather than "problems," nurses may prefer terms such as "issues," "client needs," "nursing diagnoses" or others. In different health care organizations, efforts to foster multi-disciplinary involvement in care planning may settle on different words that used in other organizations. The current embodiments includes the ability to specify locally-preferred standardized words, and then to use these words consistently throughout the application. In alternative embodiments, systems configuration and maintenance users can specify different terminology to be used by default for different groups of users, enabling the same system to be used with different terminology to support different care processes in different settings.

The method for creating and maintaining system configuration data and rules also includes step 600 for authoring and maintaining rules for permitted node-to-node hierarchical relationships based on node types and sub-types, assigning default values for node-to-node hierarchical relationship types 610, and determining which node type and sub-types can be subsumed to be displayed as if they were attributes within nodes of other types and sub-types.

Figure 14:
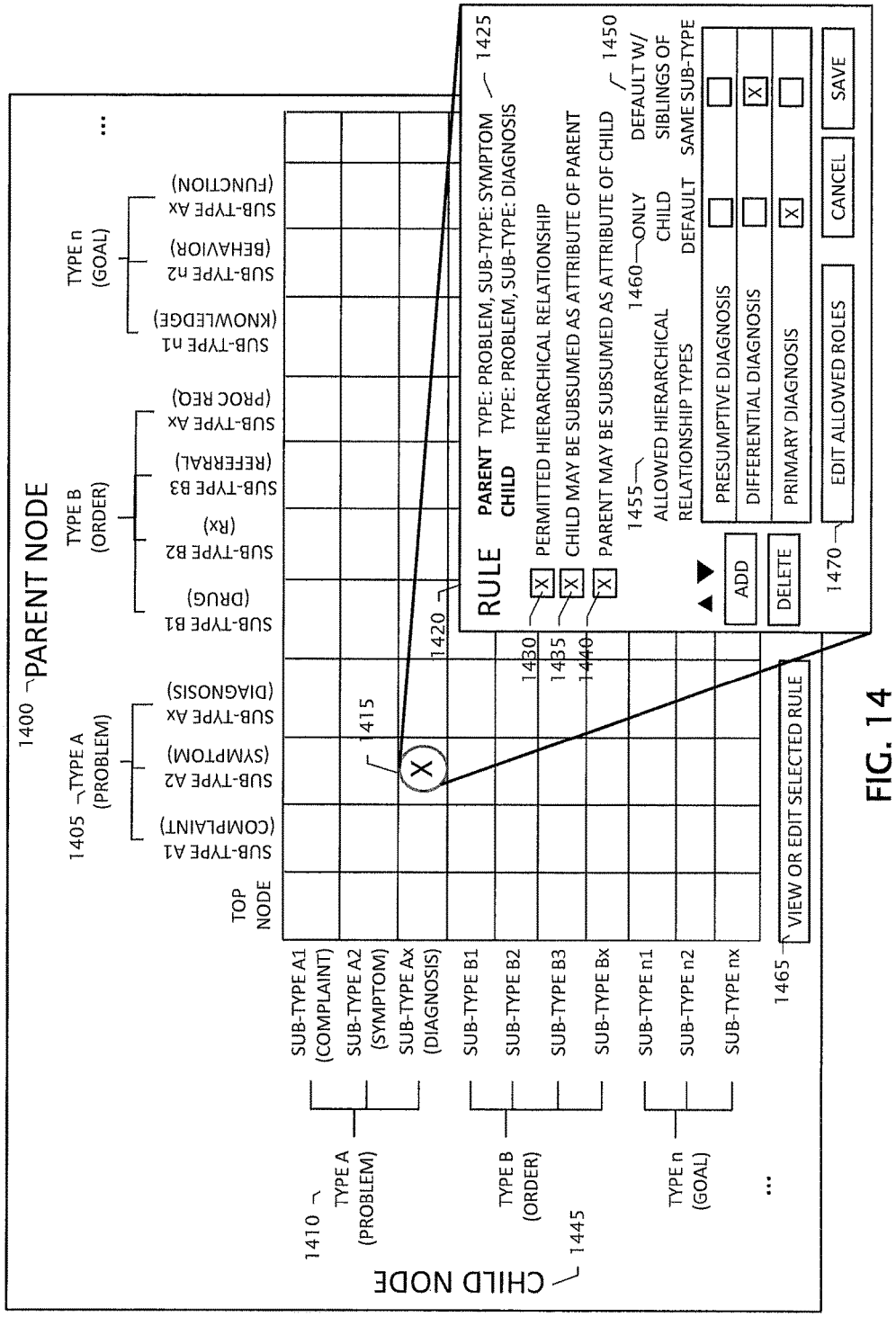
FIG. 14 is a diagram representing a user interface illustrating and example simple structure of rules regarding permitted node-to-node hierarchical relationships, relationship types and node subsumption rules

Turning to FIG. 14, a diagram is provided to provide an example of a relatively simple structure for these types of system configuration data and rules. The diagram illustrates such a structure through the depiction of a user interface intended for use to maintain that structure. The main element of this user interface is a grid with columns corresponding to types and subtypes of parent nodes 1400, with columns organized by types 1405, such as problems, and subtypes such as complains and symptoms. The rows of the grid correspond to types and sub-types of child nodes, also organized by types 1400 and sub-types. On the grid, cell 1415 corresponds to structured care plan node hierarchical relationships meeting the criteria 1425 that the parent node is of type problem, with a sub-type of symptom, and the child node is of type problem, with a sub-type of diagnosis. More succinctly, diagnoses within a symptom. By selecting the cell on the grid 1415 and then selecting button 1465 ("view or edit selected rule"), the system presents the user with a dialog box allowing the user to specify rule parameters to apply to such node-to-node hierarchical relationships within a structured care plan. In the example, check-box 1430 is checked to indicate that such a hierarchical relationship, a symptom node with a diagnosis as a child node, makes clinical sense and is permitted to exist in the structured care plan. Check-box 1435 is checked to indicate that a clinical user modifying a structured care plan will be permitted to select a diagnosis node that is a child to a symptom node and drag that diagnosis node on top of the symptom node to cause the structured sentence associated with the child node to be displayed as if it was an attribute within the structured sentence associated with the parent node. Check-box 1440 is checked to indicate that the reverse also makes clinical sense, dragging symptom node on top of a child node for a diagnosis to cause the structured sentence associated with the parent node to be displayed as if it was an attribute within the structures sentence associated with the parent. The table 1455 lists the hierarchical relationship types that are configured to be allowed for diagnosis nodes that are children to symptom nodes. The table indicates that is makes clinical sense for such node-to-node hierarchical relationship to be of types presumptive diagnosis, differential diagnosis, and primary diagnosis. Check-boxes in columns 1460 and 1450 are checked to indicate that if there are no other diagnosis codes that are siblings sharing a symptom node as a parent, that the default hierarchical relationship code of primary diagnosis should be assigned. If, however, there are more than one diagnosis nodes that are siblings under a symptom node, then the rule indicates that the hierarchical relationships types for such diagnosis codes should default to differential diagnosis. The button 1470 ("edit allowed roles") illustrates that the user can navigate to another dialog window to specify additional rules that could limit which user roles would be permitted to create or move nodes so as to create this type of hierarchical relationship among structured care plan nodes. It is understood that this illustration of a user interface, or the specific structure of the rules implied by this user interface are not intended as limiting. It is anticipated that more sophisticated rule logic that can be refined over time to seek the right balance between consistency and flexibility, permitting users to reflect their clinical thinking and emphasis without creating risk of having structured care plans devolve into structures which do not make sense clinically or that are incompatible with the ways that co-authors of the care plan want to express their own clinical thinking and emphasis.

Although the embodiments have been particularly described, it should be readily apparent to those of ordinary skill in the art that various changes, modifications and substitutes are intended within the form and details thereof, without departing from their spirit and scope. Accordingly, it will be appreciated that in numerous instances some features will be employed without a corresponding use of other features. Further, those skilled in the art will under-

The invention claimed is:

1. A method of providing patient health information corresponding to care plan elements, including such care plan elements as problems and orders, into a computer system to create an updated structured care plan for a patient, the patient health information being provided from a plurality of different external sources and operable upon by the computer system, the method comprising the steps of:
    providing, within the computer system, an application program for entry of patient health information, the application program providing for linkage between a plurality of care plan elements, a topic catalog, and a structured care plan;
    providing, from the computer system and associated with the application program, a collection of topics organized into a plurality of topic nodes within a hierarchical topic catalog, the plurality of topic nodes, at least one having an associated structured sentence template, and a plurality of such structured sentence templates being associated with a care plan template;
    instantiating, in the computer system and with the application program, the structured care plan for the patient, including a hierarchy of care plan nodes, at least one of which has a link to at least one topic node of the plurality of topic nodes in the hierarchical topic catalog and at least one of which has an associated structured sentence;
    receiving, at the computer system and associated with the application program, data from one of the plurality of different external sources, such data containing one or more problem care plan elements and one or more order care plan elements corresponding to the patient;
    matching, by the computer system and the application program, the care plan elements obtained from the external sources with the plurality of topic nodes within the hierarchical topic catalog, and identifying at least one topic node of the plurality of topic nodes for which there is an associated structured sentence template in the hierarchical topic catalog and for which there are no linked care plan nodes within the structured care plan for the patient;
    instantiating, by the computer system and the application program, within the care plan for the patient, at least one proposed node linked to the at least one topic node, the at least one proposed node having an associated including a structured sentence created based on the structured sentence template of the at least one topic node; and
    updating, using the computer system and the application program, the structured care plan into an updated structured care plan in response to confirmation of the proposed node as a new node in the updated structured care plan.

2. The method according to claim 1, further including the step of instantiating the at least one proposed node and the associated structured sentence within the structured care plan for the patient based on the corresponding plurality of structured sentence templates within the care plan template.

3. The method according to claim 2 wherein the step of instantiating the at least one proposed node includes the steps of:
    capturing clinician user input regarding whether the clinician user wants each newly instantiated structured sentence to be added to a bottom of the care plan or if the clinician user wants each newly instantiated structured sentence to be added to a first location within the node hierarchy of the care plan based on a second location of the corresponding at least one topic node within the hierarchy of the topic catalog; and
    altering the care plan node hierarchy by adding care plan nodes and associated structured sentences into the structured care plan consistent with said clinician user input.

4. The method according to claim 2, wherein the step of instantiating the at least one proposed node instantiates a plurality of proposed nodes and associated structured sentences within the structured care plan, and further includes the steps of:
    capturing clinician user input regarding whether the clinician user wants all of the plurality of proposed nodes to be displayed among other topic nodes within the hierarchy of care plan nodes within the structured care plan or if the clinician user wants all of the plurality of proposed nodes to be displayed adjacent to one another;
    displaying the structured care plan to the clinician user in accordance with the captured clinician user input;
    capturing clinician user input regarding the conversion of the plurality of proposed nodes to activated nodes or the rejection of proposed nodes;
    capturing clinician user input regarding edits to structured sentence attribute values; and
    instantiating activated care plan nodes and associated structured sentences within the care plan according to the clinician user input.

5. The method according to claim 4, wherein the step of displaying the structured care plan to the clinician user includes the steps of:
    gathering additional clinician user input regarding whether the clinician user wants the structured sentences to be displayed in a comprehensive display format that includes the display of all attributes and values within the structured sentences or if the clinician user wants the structured sentences to be displayed in a terse display format that includes only a subset of the attributes and values within the structured sentence; and
    displaying the structured care plan in a format consistent with the additional clinician user input.

6. The method according to claim 2, further including the structured sentence template having an associated plurality of smart template rules containing logic to determine whether the structured sentence template is appropriate to the patient and wherein the step of displaying the structured care plan to the clinician user includes the steps of:
    obtaining the smart template rules associated with each structured sentence template;
    obtaining the values of any patient attributes included as inputs to the smart template rules;
    applying the logic contained within the smart template rules to determine if the associated structured sentence template is appropriate to the patient; and
    including or excluding from the display of the structured care plan any care plan proposed nodes and associated proposed structured sentences corresponding to the structured sentence template based on the result of the step of applying the logic.

7. A method of providing for a plurality of clinician views of a structured care plan for a patient, the structured care plan being operable upon using a computer system, the method comprising the steps of:
    providing, within the computer system, an application program for creation and display of a structured care plan, the structured care plan including a hierarchical plurality of care plan nodes, each care plan node including an associated structured sentence;

receiving, at the computer system and associated with the application program, a first set of clinician-specific view tailoring instructions corresponding to a particular structured care plan for a particular patient, each of the clinician-specific view tailoring instructions corresponding to particular nodes or particular node-to-node relationships within the structured care plan and specifying a constrained set of operations on the hierarchical plurality of nodes, wherein the constrained set of operations includes one of changing the order of sibling nodes, changing node-to-node hierarchical relationships, subsuming a node within a parent or child node, demoting a node and changing the display prominence of a node;

at least one of the clinician-specific view tailoring instructions specifying an operation performed by the computer system and with the application program to change a node-to-node hierarchical relationship and thereby updating a clinician-specific representation of the structured care plan to associate therewith the first set of clinician-specific view tailoring instructions, the updating including the step of propagating at least one of such clinician-specific view tailoring instructions to other ones of the plurality of clinician views if the one such clinician-specific view tailoring instruction was created by a clinician having a primary care relationship with the patient or if the one such clinician-specific view tailoring instruction was applied to care plan nodes or node-to-node hierarchical relationships that correspond to problems for which the clinician has care responsibility or to descendent nodes of such problem nodes; and wherein during the updating of the clinician-specific representation of the structured care plan, node to node relationships within the hierarchical plurality of nodes are altered.

8. A method according to claim 7, wherein the first set of clinician-specific view tailoring instructions are created and stored based on user interactions with the structured care plan, said user interactions corresponding to the constrained set of operations.

9. The method according to claim 7, wherein the step of receiving the first set of clinician-specific view tailoring instructions includes receiving a plurality of rules that are used by the computer system and the application program to generate certain ones of the clinician-specific view tailoring instructions based on patient-specific information.

10. The method according to claim 9, wherein the patient-specific information includes at least one of characteristics of a particular clinician user, the care relationship between the particular clinician user and the patient, and the care responsibility relationship between the particular clinician user and the problems within the structured care plan.

11. The method according to claim 7, wherein the step of receiving the first set of rules includes receiving rules based on patient-specific information that are used by the computer system and the application program to determine the clinician-specific view tailoring instructions that apply to a clinician-specific representation of the structured care plan for a particular clinician user and the clinician view generated for the particular clinician user.

12. The method according to claim 11, wherein the patient-specific information includes at least one of characteristics of the particular clinician user, the care relationship between the particular clinician user and the patient, and the care responsibility relationship between the particular clinician user and the problems within the structured care plan.

13. The method according to claim 7, wherein the step of propagating includes the steps of:

analyzing clinician-specific view tailoring instructions for each of the plurality of clinician views;

selecting a subset of the analyzed clinician-specific view tailoring instructions and associating the subset with a particular clinician user;

generating the clinician-specific representation of the structured care plan with changes to the hierarchy of care plan nodes and including data elements specifying display prominence characteristics of the care plan nodes, consistent with the constrained set of operations specified by the subset of clinician-specific view tailoring instructions; and providing a display of the clinician-specific representation of the structured care plan to the particular clinician user, the display being consistent with the hierarchy of care plan nodes and the display prominence of nodes in the clinician-specific representation.

14. The method according to claim 13, where the step of generating the clinician-specific representation of the structured care plan includes the steps of:

generating the clinician-specific representation at a time changes are made to any clinician-specific view tailoring instructions associated with the structured care plan; and storing the clinician-specific representation in a database.

15. The method according to claim 13, where the step of generating the clinician-specific representation of the structured care plan is executed when the particular clinician user requests the display of the clinician-specific view of the structured care plan.

16. The method according to claim 7, further including the step of specifying care relationship data that is operated upon by the computer system and the application program said care relationship data documenting types of care relationships that exist during specified periods of time between specified health care providers and a patient.

17. The method according to claim 16, wherein the care relationship data is associated with a particular structured care plan for the patient, such that the care relationship data for the structured care plan for the patient is shared for use by each of the plurality of clinician-specific views of the structured care plan.

18. The method according to claim 16, wherein the care relationship data is associated with the patient, such that the care relationship data for the patient is shared for use by each of a plurality of clinician views of each of a plurality of structured care plans for the patient.

19. The method according to claim 16, further including the step of deriving the care relationship data, the step of deriving the care relationship data including the steps of:

obtaining external data;

applying a set of rules to the external data to derive the care relationship data; and storing the derived care relationship data in the database.

20. The method according to claim 19, wherein the external data is claims data.

21. The method according to claim 7, further including the step of specifying care responsibility data that is operated upon by the computer system and the application program, said care responsibility data documenting, as part the structured care plan, types of care responsibilities that exist during specified periods of time between specified health care providers and specified problem nodes for the patient.

22. The method according to claim 21, further including the step of deriving the care responsibility data, the step of deriving the care responsibility data including the steps of:
obtaining external data;
obtaining other care responsibility data from other structured care plans for the patient;
applying a set of rules to the external data and the other care responsibility data from other structured care plans to derive the care responsibility data; and
storing the derived care responsibility data in the database as part of the structured care plan.

23. The method according to claim 22, wherein the external data is claims data.

24. The method according to claim 22, wherein the step of specifying the types of care responsibilities includes the steps of:
checking to determine if the corresponding problem is already contained within the structured care plan in the form of a problem node; and
if so, associating the care responsibility with the existing problem node within the structured care plan; and
if not, instantiating a proposed problem and associating the care responsibility with this proposed problem within the structured care plan.

25. The method according to claim 22, further including the step of providing an alert to the clinician user specified in care responsibility data within the structured care plan when there are one or more conflicts such that the clinician user specified in the structured care plan to have care responsibility during a particular time period for a particular problem is different than the clinician user specified to have care responsibility during an overlapping time period for the particular problem within other structured care plans for the same patient or when there are the one or more conflicts between the care responsibilities derived based on applying rules to external data and the care responsibility data within a structured care plan.

* * * * *